United States Patent [19]  [11] Patent Number: 4,959,362
Terao et al.  [45] Date of Patent: Sep. 25, 1990

[54] PHARMACEUTICAL COMPOSITIONS CONTAINING CERTAIN ASCORBIC ACID DERIVATIVES USEFUL IN THE PROPHYLAXIS AND TREATMENT OF DISORDERS OF THE CIRCULATORY SYSTEM

[75] Inventors: Shinji Terao, Toyonaka; Minoru Hirata, Ikeda, both of Japan

[73] Assignee: Takeda Chemical Industries, Inc., Osaka, Japan

[21] Appl. No.: 245,943

[22] Filed: Sep. 19, 1988

Related U.S. Application Data

[63] Continuation of Ser. No. 863,429, May 15, 1986, abandoned, which is a continuation-in-part of Ser. No. 683,136, Dec. 18, 1984, abandoned.

[30] Foreign Application Priority Data

Dec. 19, 1983 [JP] Japan ........................... 58-240741
May 17, 1985 [WO] PCT Int'l Appl. ... PCT/JP85/00272
Jun. 18, 1985 [WO] PCT Int'l Appl. ... PCT/JP85/00340

[51] Int. Cl.$^5$ ............... A61K 31/455; A61K 31/535; A61K 31/40; A61K 31/34
[52] U.S. Cl. ................................. 514/231.5; 549/59; 549/60; 549/315; 546/283; 546/256; 544/152; 514/333; 514/336; 514/338; 514/422; 514/444; 514/464; 514/467; 514/474
[58] Field of Search ................ 549/315; 546/283; 514/231.5, 422, 444, 474, 464, 467, 333, 338, 336

[56] References Cited

U.S. PATENT DOCUMENTS 4,552,888 11/1985 Koppel et al. ................. 514/474

FOREIGN PATENT DOCUMENTS

A14684840 12/1968 Fed. Rep. of Germany ...... 549/315
A1518988 12/1969 Fed. Rep. of Germany ...... 549/315
A27299 1/1978 Fed. Rep. of Germany ...... 549/315
0074411 3/1983 Fed. Rep. of Germany ...... 549/315

OTHER PUBLICATIONS

European Search Report No. 86 10 6521 dated 17 Aug. 87.
Lu et al., J. Agric. Food Chem. vol. 32, pp. 21-28, 1984.
Chemical Abstracts, 69, No. 66921g, 1968.
Chemical Abstracts, 83, No. 179514j, 1975
Chemical Abstracts, 75, No. 130075n, 1971.
Chemical Abstracts, 73, No. 99173a, 1970.
Chemical Abstracts, 103, No. 27082k, 1985.
Chemical Abstracts, 102, No. 27082k, 1985.
Chemical Abstracts, 102, No. 165694s, 1985.
Niki et al., Chemical Letters, pp. 631-632, 1983, The Role of Vitamin C as an Antioxidant.
J. M. McCord, Oxygen-Derived Free Radicals in Postichemic Tissue Injury, The New England Journal of Medicine, vol. 312, No. 3, 1985.
J. Org. Chem., 50, 281-283, 1985.
Remington's Pharmaceutical Sciences, 14th Edition, pp. 1666-1668, Mack Publishing Company (1970).

Primary Examiner—Alan L. Rothman
Attorney, Agent, or Firm—Wegner & Bretschneider

[57] ABSTRACT

An ascorbic acid derivative of the formula:

$$\begin{array}{c} R^3-O \\ R^2 \end{array} \underset{HO}{\overset{O}{\bigvee}} \underset{O-R^1}{\overset{=O}{}} \quad [I]$$

wherein $R^1$ is organic residue having molecular weight of from 15 to 700, $R^2$ is hydrogen or hydroxyl, $R^3$ is hydrogen, acyl, optionally substituted phosphono or sulfo, and $R^3$ and hydroxyl or $R^2$ may form acetal residue or ketal residue, and a salt thereof are provided.

The compound [I] and salts thereof have antioxidant activity and excellent prophylactic and improving actions on disorders of circulatory functions, and they are usefule as antioxidant agent for food and as agents of prophylaxis and improvement of circulatory functional disorders.

18 Claims, 1 Drawing Sheet

PHARMACEUTICAL COMPOSITIONS CONTAINING CERTAIN ASCORBIC ACID DERIVATIVES USEFUL IN THE PROPHYLAXIS AND TREATMENT OF DISORDERS OF THE CIRCULATORY SYSTEM

This application is a continuation of U.S. application Ser. No. 863,429, filed May 15, 1986, now abandoned, which is a continuation-in-part of U.S. application Ser. No. 683,136, filed Dec. 18, 1984, now abandoned.

This is a continuation-in-part of Ser. No. 683,136, filed on Dec. 18, 1984.

The present invention relates to an ascorbic acid derivative, its production and use.

Ascorbic acid possesses oxidation preventive activity, and is used in foods for the purposes of prevention of browning, retention of flavor, preservation of freshness, and the like.

However, ascorbic acid is susceptible to degradation, and encounters in some instances difficulties in producing the above-mentioned effect over a prolonged period of time.

Under these circumstances, the present inventors conducted extensive research with a specific view to obtaining an ascorbic acid derivative which is less susceptible to degradation and also possesses adequate oxidation preventive activity, and as a result, found that modification of the 2-position of ascorbic acid with a group having a relatively large molecular weight can yield a compound which achieves the desired object. The finding was followed by further research, which has culminated in the present invention.

Diseases of heart, brain, kidney, etc., which are often observed in adults, are mainly caused by disturbances and destruction of cells or tissues due to ischemia as a basal pathologic state, to result in hemostasia leading to suspension of supplying energy source. The morbidity rate of, for example, ischemic heart diseases, ischemic cerebral diseases, ischemic renal disturbances, ischemic gastrointestinal ulcers, has recently increased with the development of highly civilized society, and of the society holding high rates of persons of advanced age, and these diseases have become major factors in mortality rate in advanced countries.

Recently, it has been revealed that biologically activated oxygen species or reactive organic radical species play an important role in aggravation of lesions in ischemic tissues (i.e. lowering of cell function, disturbances, destruction, necrosis of cells, etc.) [I. Fridovich, Annual Review of Pharmacology and Toxicology 23, 239 (1983); J. M. McCord, The New England Journal of Medicine, 312, 159 (1985); K. P. Burton, J. M. McCord and G. Ghai, American Journal of Physiology, 246, H776 (1984)]. As the active oxygen species or reactive organic radical species in living system are considered, among others, superoxide anion radical ($O_2^-$), hydroxyl radical (.OH), singlet oxygen ($^1O_2$), and peroxide radical (ROO.). Especially, relationship between the formation of $O_2^-$ in a living system and the subsequent damages of cells or tissues caused by the reactive oxygen specieses have important meanings in ischemic disorders. Especially, it is considered that excess generation of $O_2^-$ in developing tissue damages after blood reperfusion at the site of ischemic lesion or after ischemia has an important significance.

It has been known that superoxide dismutase effectively acts to scavenge $O_2^-$ specifically, protects against tissue damages and alleviates tissue disturbances after reperfusion of the site of ischemia or after ischemia [D. N. Granger, G. Rulili, J. M. McCord, Gastroenterotogy, 81, 22 (1981)]. Also, it has been reported that such compounds as ascorbic acid, α-tocopherol, cysteine and reduced glutathione have an activity to scavenge free radicals, and that these compounds could prevent lesions in tissues, which are seemed to be caused by free radicals in pathological conditions [I. Fridovich, Science, 201, 875 (1978)].

Based on the fundamental studies so far made, revealing that reactive oxygen species and organic radicals play a significantly important role in causing tissue disturbances in a living system, the present inventors have conducted research work for finding out a novel type of pharmaceuticals excellent pharmacologically as well as pharmaceutically aiming at scavenging reactive oxygen species and organic radicals. As the result, the present inventors found that 2-O-substituted ascorbic acid derivatives and homologs thereof showed, in experiments in vitro and in various animal test models, strong actions to scanvenge reactive oxygen species and organic radicals, and that they controlled ischemic heart diseases, distrubances in cerebral function or renal disorders, thus accomplishing the present invention.

The present invention relates to an ascorbic acid derivatives of the formula;

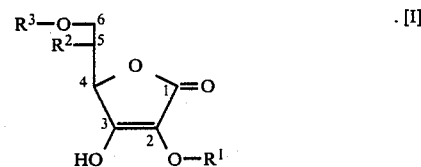

wherein $R^1$ stands for an organic residue having a molecular weight of from 15 to 700; $R^2$ stands for hydrogen or hydroxyl group; and $R^3$ stands for hydrogen, acyl group or an optionally substituted phosphono group, and $R^3$ and the hydroxyl group of $R^2$ may form acetal residue or ketal residue; provided that $R^1$ is other than methyl when $R^2$ is hydroxyl and $R^3$ is hydrogen] and a salt thereof, a method for producing an ascorbic acid derivative representable by the general formula;

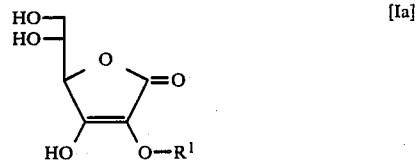

[wherein $R^1$ stands for a molecular weight of from 29 to 700] or a salt thereof, characterized by subjecting a compound representable by the formula;

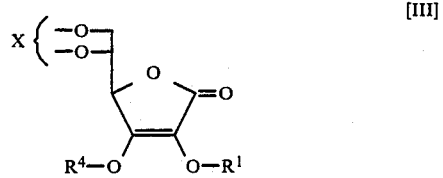

[wherein $R^1$ is as defined above; $R^4$ stands for a group cleavable by hydrolysis or reduction; and X stands for two hydrogens, acetal residue or ketal residue] to hydrolysis or acid hydrolysis, followed by reduction, a method for producing an ascorbic acid derivative representable by the general formula;

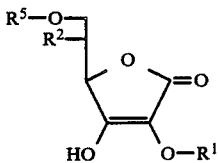
[Ib]

[wherein $R^1$ and $R^2$ are as defined above; and $R^5$ stands for acyl or optionally substituted phosphono] characterized by subjecting an ascorbic acid derivative representable by the general formula;

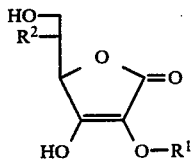
[IV]

[wherein $R^1$ and $R^2$ are as defined above] to acylation or phosphorylation, and in case of acylation being conducted, followed by, when necessary, acyl migration or deacylation, a method for producing an ascorbic acid derivative representable by the formula;

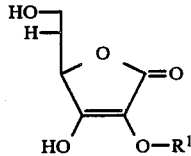
[Ic]

[wherein $R^1$ is as defined above], characterized by subjecting a compound representable by the formula;

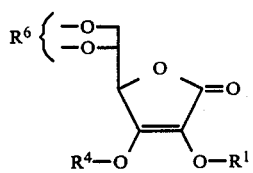
[V]

[wherein $R^1$ and $R^4$ are as defined above; and $R^6$ stands for acetal residue, ketal residue or O=S< group] to dehydration, then reduction, followed by, when necessary, hydrolysis, a method for producing an ascorbic acid derivative representable by the formula;

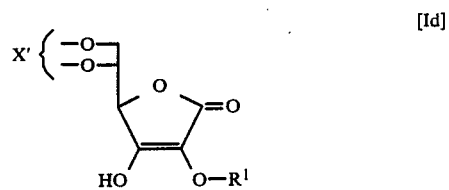
[Id]

[wherein X' stands for acetal residue or ketal residue, and $R^1$ is as defined above] characterized by subjecting an ascorbic acid derivative representable by the formula;

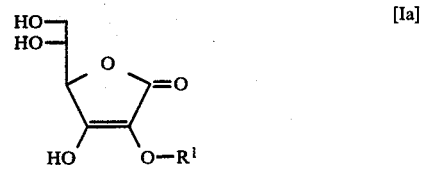
[Ia]

[wherein $R^1$ is as defined above] to acetalization or ketalization, and an antioxidant preparation for food or a pharmaceutical composition for prophylaxis and improvement of disorders in functions of the circulatory system, which contains an ascorbic acid derivatives of the formula;

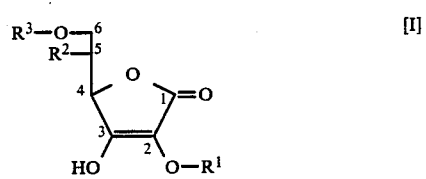
[I]

[wherein $R^1$ stands for an organic residue having a molecular weight of from 15 to 700; $R^2$ stands for hydrogen or hydroxyl group; and $R^3$ stands for hydrogen, acyl group, an optionally substituted phosphono group or sulfo group, and $R^3$ and the hydroxyl group of $R^2$ may form acetal residue or ketal residue], or a salt thereof, and a carrier, vehicle or diluent therefor.

Among the compound [I], preferable compound is a compound of the formula:

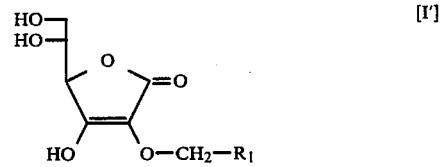
[I']

wherein $R^1$ is an organic residue having a molecular weight of from 58 to 400.

In the above formula [I'], the organic residue having a molecular weight of from 58 to 400 as represented by $R_1$ includes, for example, straight-chain or branched alkyl groups, straight-chain or branched alkyl groups which have a substituent or substituents, alkenyl groups which may have a substituent or substituents, aryl groups which may have a substituent or substituents, aralkyl group which may have a substituent or substituents, acyl groups which may have a substituent or substituents, aryloxy groups which may have a substituent or substituents and aralkyloxy groups which may have a substituent or substituents.

The above straight-chain or branched alkyl group having a molecular weight of from 58 to 400 is preferably those having 5 to 22 carbon atoms, more preferably those having 9 to 20 carbon atoms.

Examples of such alkyl groups include, for example, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosyl, n-heneicosyl and n-docosyl.

The alkyl in the above straight-chain or branched-chain alkyl groups having a molecular weight of from 58 to 400 which have a substituent or substituents is preferably those having 1 to 10 carbon atoms.

Examples of the said alkyl group include, for example, methyl, ethyl, n-propyl, isopropyl, n-butyl, isobutyl, sec-butyl, tert-butyl, n-pentyl, n-hexyl, n-heptyl, n-octyl, n-nonyl and n-decyl.

The above substituent includes, for example, lower alkoxycarbonyl groups, aryl groups which may have a substituent or substituents, aralkyl groups which may have a substituent or substituents, arylcarbonyloxy groups which may have a substituent or substituents, aralkylcarbonyloxy groups which may have a substituent or substituents, 2,3,5-trimethyl-1,4-benzoquinoyl group, 2,3-dimethoxy-5-methyl-1,4-benzoquinoyl group and 2-methyl-1,4-naphthoquinoyl group.

The alkoxy in the said lower alkoxycarbonyl groups is preferably those having 1 to 6 carbon atoms, and examples of such alkoxy groups includes, for example, methoxy, ethoxy, n-propoxy, n-butoxy, n-pentoxy and n-hexoxy.

The aryl group in said aryl groups which may have a substituent or substituents and in said arylcarbonyloxy groups which may have a substituent or substituents includes, for example, phenyl, naphthyl, thienyl and furyl. The aralkyl group in said aralkyl groups which may have a substituent or substituents and in said aralkylcarbonyloxy groups which may have a substituent or substituents includes, for example, benzyl and phenethyl. The substituent for such aryl group or aralkyl groups includes, for example, lower alkyl of 1 to 5 carbon atoms (e.g., methyl, ethyl, n-propyl, isopropyl, n-butyl, sec-butyl, tert-butyl, n-pentyl, etc.), lower alkoxy of 1 to 3 carbon atoms (e.g., methoxy, ethoxy, propoxy, etc.), halogen (e.g., chlorine, bromine, iodine, fluorine, etc.), nitro, amino, oxo, hydroxyl and benzyloxy.

The alkenyl group in the above alkenyl groups having a molecular weight of from 58 to 400 which may have a substituent or substituents is preferably those having 2 to 20 carbon atoms, and examples of such alkenyl groups include, for example, vinyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl and eicosenyl, with the substituent for such alkenyl groups including for example aryl groups (e.g., phenyl, naphthyl, etc.), aralkyl (e.g. benzyl, phenethyl, etc.) and 5- or 6-membered heterocyclic groups (e.g., 3-pyridyl, thienyl, furyl, etc.).

The aryl group in the above aryl groups having a molecular weight of from 58 to 400 which may have a substituent or substituents includes, for example, phenyl and naphthyl. The substituent for such aryl groups includes, for example, alkyl groups of 1 to 5 carbon atoms (e.g., methyl, ethyl, n-propyl, isopropyl, n-butyl, isobutyl, sec-butyl, tert-butyl, n-pentyl, etc.), and methoxy, methylenedioxy and hydroxyl groups.

The aralkyl group in the above aralkyl groups having a molecular weight of from 58 to 400 which may have a substituent or substituents includes, for example, benzyl and phenethyl. The substituent for such aralkyl groups includes, for example, alkyl groups of 1 to 5 carbon atoms (e.g., methyl, ethyl, n-propyl, isopropyl, n-butyl, isobutyl, sec-butyl, tert-butyl, n-pentyl, etc.), and methoxy, methylenedioxy and hydroxyl groups.

The acyl group in the above acyl groups having a molecular weight of from 58 to 400 which may have a substituent or substituents is preferably those having 1 to 9 carbon atoms, and examples of such acyl groups include, for example, formyl, acetyl, propionyl, butyryl, isobutyryl, benzoyl, morpholinocarbonyl, $C_{1-3}$alkoxycarbonylpyrrolidinocarbonyl (e.g., 2-methoxycarbonylpyrrolidinocarbonyl, 2-propoxycarbonylpyrrolidinocarbonyl, etc.), $C_{1-3}$alkoxycarbonyl (e.g., methoxycarbonyl, ethoxycarbonyl, propoxycarbonyl, etc.), arylcarbonyl which may have a substituent or substituents and aralkylcarbonyl which may have a substituent or substituents.

The aryl in the above arylcarbonyl which may have a substituent or substituents includes, for example, phenyl and naphthyl. The aralkyl in the above aralkylcarbonyl which may have a substituent or substituents includes, for example, benzyl and phenethyl. The substituent for such aryl or aralkyl includes, for example, hydroxyl, lower alkyl of 1 to 5 carbon atoms (e.g., methyl, ethyl, n-propyl, isopropyl, n-butyl, isobutyl, tert-butyl, n-pentyl, etc.) and lower alkoxy of 1 to 3 carbon atoms (e.g., methoxy, ethoxy, propoxy, etc.).

The aryl in the above aryloxy groups having a molecular weight of from 58 to 400 which may have a substituent or substituents includes, for example, phenyl, naphthyl, thienyl and furyl, and examples of the substituent include, for example, hydroxyl group, lower alkyl of 1 to 5 carbon atoms (e.g., methyl, ethyl, n-propyl, isopropyl, n-butyl, sec-butyl, tert-butyl, n-pentyl, etc.) and lower alkoxy of 1 to 3 carbon atoms (e.g., methoxy, ethoxy, propoxy, etc.).

The aralkyl in the above aralkyloxy groups having a molecular weight of from 58 to 400 which may have a substituent or substituents includes, for example, benzyl and phenethyl, and examples of the substituent include, for example, hydroxyl group, lower alkyl of 1 to 5 carbon atoms (e.g., methyl, ethyl, n-propyl, isopropyl, n-butyl, sec-butyl, tert-butyl, n-pentyl, etc.) and lower alkoxy of 1 to 3 carbon atoms (e.g., methoxy, ethoxy, propoxy, etc.).

The acyl group representable by $R^3$ in the above general formulae include straight-chain or branched fatty acid whose carbon number is $1\sim 22$, optionally substituted benzoic acid, optionally substituted thienylacetic acid, optionally substituted phenylacetic acid, dicarboxylic acid, acyl groups derivable from carboxylic acid representable by the formulae;

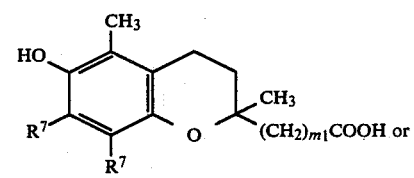

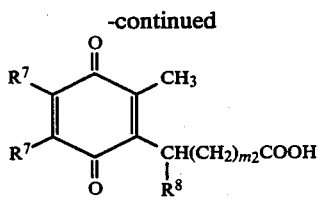

[wherein $R^7$ stands for methyl group, methoxy group, and the two $R^7$'s form —CH=CH—CH=CH— group; and $R^8$ stands for phenyl, naphthyl, thienyl or pyridyl, m, denotes an integer of 1 or 2 and $m_2$ denotes an integer of 2 to 8] or an optionally substituted aminocarbonyl group.

Examples of the fatty acid include $C_{1-20}$ fatty acid of formic acid, acetic acid, propionic acid, valeic acid, butyric acid, hexanoic acid, heptanoic acid, octanoic acid, nonanoic acid, decanoic acid, undecanoic acid, tridecanoic acid, tetradecanoic acid, pentadecanoic acid, hexadecanoic acid, octadecanoic acid, nonadecanoic acid, eicosanoic acid, isopropionic acid, etc.

Examples of the substituents of the said optionally substituted benzoic acid include $C_{1-3}$ alkyl, $C_{1-3}$ alkoxy, methylenedioxy, halogen, etc. The substituent of the optionally substituted 2- or 3-thienyl acetic acid is exemplified by $C_{1-3}$ alkyl. Examples of the substituent of the optionally substituted phenyl acetic acid include $C_{1-3}$ alkyl, $C_{1-3}$ alkoxy, methylenedioxy, halogen, etc. The substituents of the optionally substituted phenyl group thienyl group or naphthyl group representable by $R^{17}$ are exemplified by $C_{1-3}$ alkyl, $C_{1-3}$ alkoxy, methylenedioxy, halogen, etc. The substituent of the said optionally substituted aminocarbonyl group is exemplified by optionally mono- or di-substituted $C_{1-6}$ lower alkyl group or monophenyl group. Examples of the $C_{1-6}$ lower alkyl group include methyl, ethyl, n-propyl, isopropyl, n-butyl, isobutyl, n-pentyl, n-hexyl, etc. The substituents are exemplified by phenyl, naphthyl, pyridyl, imidazolyl, etc.

As the acyl group derivable from dicarboxylic acid is mentioned those of monoester type. Examples of the dicarboxylic acid include malonic acid, succinic acid, glutaric acid, adipic acid, etc.

As the said $C_{1-6}$ lower alkyl are exemplified methyl, ethyl, n-propyl, isopropyl, n-butyl, n-pentyl, n-hexyl, etc.

As the said $C_{1-3}$ alkyl are exemplified methyl, ethyl, n-propyl, isopropyl, etc.

As the said alkoxy are exemplified methoxy, ethoxy, n-propoxy, isopropoxy, etc.

As the said halogen are exemplified chlorine, bromine, iodine and fluorine. In the above formulae, the substituents at the optionally substituted phosphono group as represented by $R^3$ are preferably mono-substituted ones which are exemplified by those representable by the formula —$(CH_2)_n$-$R^{24}$ [wherein n denotes an integer of 1-3 and $R^{24}$ stands for a heterocyclic group having amino, dialkylamino, trialkylamino or nitrogen].

Preferable examples of the alkyl at the dialkylamino and trialkylamino as represented by $R^{24}$ are methyl, ethyl, n-propyl and isopropyl.

As the nitrogen-containing heterocyclic ring as represented by $R^{24}$ are exemplified 1-pyridinio, 1,3-thiazolinio, piperazinyl, piperidino, morpholino, pyrrolidinyl, etc.

In the above general formula, examples of the cleavable groups by hydrolysis as represented by $R^4$ are methoxymethyl, ethoxymethyl, benzyloxymethyl, 2-tetrahydropyranyl, trimethylsilyl, dimethyl tertiary butylsilyl, etc., and examples of the cleavable groups by reduction as represented by $R^4$ are benzyl, p-methoxybenzyl, etc.

As the above-mentioned acetal residue, groups representable by the formula $R^{21}$—CH< [wherein $R^{21}$ stands for $C_{1-3}$ alkyl, phenyl or p-methoxyphenyl] are mentioned, and, as the ketal residue, groups representable by the formula

[wherein $R^{22}$ and $R^{23}$ independently stand for hydrogen or $C_{1-3}$ alkyl, or $R^{22}$ and $R^{23}$ form —$(CH_2)_a$— (wherein a denotes 4 or 5)] are mentioned.

Examples of the above-mentioned $C_{1-3}$ alkyl include methyl, ethyl, n-propyl or isopropyl.

In case where Compound [I] or [II] is capable of forming a salt, it may be formed into a salt, and the salt is exemplified by inorganic salt of sodium salt, potassium salt, ammonium salt, hydrochloride, sulfate, etc., or it may form an internal salt.

Compound [Ia] i.e. Compound [I] wherein $R^2$ is hydroxyl group and $R^3$ is hydrogen, when the protecting group in Compound [III] is cleavable by hydrolysis, can be produced by subjecting Compound [Ia] to acid hydrolysis to remove the acetal residue or ketal residue at the 5-, and 6-positions and the protecting group at the 3-position simultaneously.

In case where the protecting group $R^4$ at the 3-position of Compound [III] is cleavable by reduction, Compound [Ia] can be produced by subjecting Compound [III] to acid hydrolysis to remove the acetal residue or ketal residue at the 5,6-position, followed by removing the protecting group at the 3-position by catalytic reduction.

Compound [Ib], i.e. Compound [I] wherein $R^3$ is acyl group, can be produced by subjecting Compound [IV], i.e. Compound [I] wherein $R^3$ is hydrogen, to acylation, or, when a compound representable by the general formula;

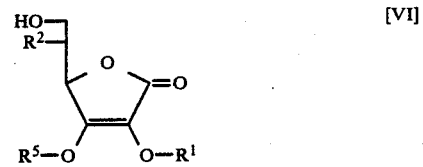

[wherein $R^1$, $R^2$ and $R^5$ are as defined above, and $R^5$ stands for acyl group] is produced by the acylation, by further subjecting the compound to acyl-rearrangement reaction. Compound [Ic], i.e. Compound [I] wherein $R^2$ and $R^3$ are both hydrogen, can be produced by subjecting Compound [V] to hydrolysis under basic conditions, followed by catalytic reduction and, when necessary, acid hydrolysis.

The above acid hydrolysis is carried out for about 1-2 hours at about 10°-80° C. in water or an organic solvent e.g. methanol, ethanol, dioxane, tetrahydrofuran, 1,2-dimethoxyethane, or an aqueous mixture thereof.

The above catalytic reduction is carried out for about 4–10 hours at about 10° C.–100° C. in an organic solvent e.g. methanol, ethanol, ethyl acetate, dioxane, 1,2-dimethoxyethane, etc., in the presence of, for example, palladium, palladium-carbon, platinum black, palladium chloride, platinum oxide, etc.

In the above acylation, as the reactivity of the enolic hydroxyl group at the 3-position is higher than that at the 6-position, the former hydroxyl group is first acylated. The 3-O-acyl derivative is, depending on the kinds of acyl group, readily rearranged internally under weakly basic conditions, to lead to a 6-O-acyl derivative [VI]. 3-O-Acyl derivative [VI] exists as an intermediate as well, but it is readily susceptible to internal migration or hydrolysis, thus being chemically unstable compound. Accordingly, a 6-O-acyl derivative can be produced by subjecting a 3-O-acyl derivative to internal migration. The internal migration completes in about 1–10 hours at about 20°–100° C. in the presence of a weak base [e.g. pyridire, sodium carbonate, buffer solution (pH about 7–8)].

The above acylation is usually conducted by a conventional method. As the solvent is often used acid chloride or anhydride of carboxylic acid (including mixed acid anhydride), and the reaction is carried out in the presence of a base e.g. pyridine, triethylamine, potassium carbonate, sodium carbonate, sodium hydrogencarbonate, etc., at about $-10°--50°$ C. The reaction time is, in most cases, within about 1–10 hours.

In the above phosporylation, the phosphorylating agent to be employed is exemplified by 2-cyanoethylphosphatedicyclohexylcarbodiimide, di-p-nitrobenzylphosphorylchloride, dioxane diphosphate, dimorpholyl phosphoric acid chloride, pyrophosphoryltetrachloride, etc.

In the above sulfonation, the surfonating agent to be employed is exemplified by sulfuric anhydride ($SO_3$), sulfuric anhydride pyridine ($SO_3-C_5H_5N$), sulfuric acid dioxane ($SO_3OC_4H_8O$), sulfuric anhydride dimethylformamide [$SO_3-HCON(CH_3)_2$], sulfuric anhydride triethylamine [$SO_3-N(C_2H_5)_3$], etc.

In the above phosphorylation and sulfonation, the solvent to be employed is exemplified by dioxane, dimethylformamide, chloroform, methylene chloride, etc. The reaction temperature is within the range of from $-10°$ C. to $-50°$ C., and the reaction time is about 1–10 hours. To lead the compound obtained to a salt thereof, a conventional means is employed. Elimination of the acyl group at the 3-position is conducted by the addition of an equimolar amount of sodium hydrogencarbonate or pyridine, and hydrolysis is conducted at room temperature. The reaction time is about 1–6 hours.

The dehydration is completed in about 1–4 hours at a temperature range of about 30°–80° C. in an organic solvent such as methylene chloride, chloroform, dioxane, tetrahydrofuran, benzene, etc., in the presence of an organic base e.g. 1,5-diazabicyclo[4,3,0]-5-nonene, 1,4-diazabicyclo[2,2,2]octane, 1,8-diazabicyclo[5,4,0]-7-undecene, pyridine, triethylamine.

By conducting the dehydration, a compound of the general formula [VI'];

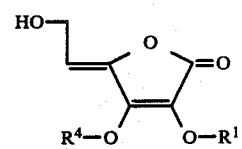

[wherein $R^1$ and $R^4$ are as defined above] can be obtained.

By subjecting compound [VI'] to reduction, followed by, when necessary, hydrolysis, Compound [Ic] can be produced. The said reduction and hydrolysis can be conducted as mentioned above.

The reaction for producing Compound [Id] by acetalization or ketalization of Compound [Ia] is conducted by allowing the starting compound to react with ketone or aldehyde, e.g. acetone, benzaldehyde, cyclopentanone, cyclohexanone, etc. As the reaction solvent are employed toluene, tetrahydrofuran, chloroform, diethylether, dichloromethane, dichloroethane, etc. The reaction temperature ranges from about 15° C. to 150° C., and the reaction is conducted in the presence of an acid catalyst. The catalyst is exemplified by acetylchloride, sulfuric acid, p-toluenesulfonic acid, camphorsulfonic acid. The reaction time ranges from about 1 to 24 hours.

Thus produced ascorbic acid derivatives [I] can be separated and collected by per se known separation and purification means (e.g. column chromatography using silica-gel, polystyrene resins, activated carbon, reverse phase system, etc., recrystallization, etc.).

Compounds employable as the starting materials in the method of this invention can be produced by, for example, the following reaction steps.

[A]- Method for producing Compound [III'], i.e. Compound [III] wherein X is acetal or ketal residue, and Compound [V'], i.e. Compound [V] wherein $R^6$ is acetal residue or ketal residue:

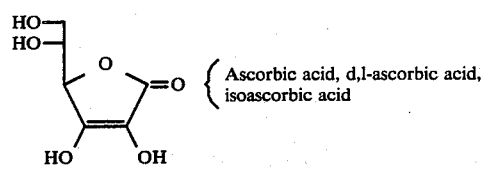

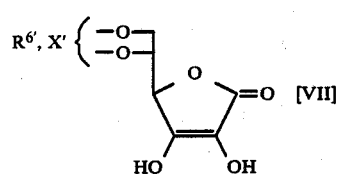

-continued

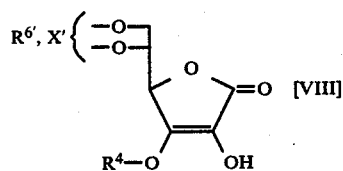
[VIII]

↓ R¹—Z

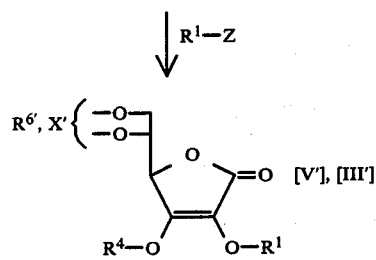
[V'], [III']

In the above formulae, X' and R⁶' stand for acetal or ketal residue.

In case of ascorbic acid being used as the starting material, the ascorbic acid is first acetalized or ketalized to produce Compound [VII]. This reaction is conducted by allowing ascorbic acid to react with ketone or aldehyde e.g. acetone, benzaldehyde, cyclopentanone, cyclohexanone, etc. As the reaction solvent are employed, among others, tetrahydrofuran, chloroform, diethylether, dichloromethane or dichloroethane. The reaction temperature ranges from room temperatures to 60° C., and the reaction is conducted in the presence of an acid catalyst. Examples of the catalyst include acetylchloride, sulfuric acid, p-toluenesulfonic acid and camphorsulfonic acid. The reaction time ranges from 4 to 24 hours. Subsequently, Compound [VII] is allowed to react with a compound representable by the formula; R⁴-Y [wherein R⁴ is as defined above, and Y stands for halogen (e.g. chlorine, bromine)] (e.g. chloromethylmethylether, chloromethylethylether, benzylchloride, benzylbromide) in dimethylformamide, dimethylsulfoxide (DMSO), hexamethylphosphoramide or tetrahydrofuran, either singly or a solvent mixture thereof in the presence of an inorganic base such as potassium carbonate, sodium carbonate, sodium hydroxide, potassium hydroxide and sodium hydrogencarbonate to produce Compound [VIII]. The reaction temperature ranger from 0° C. to 40° C. (preferably 25° C.). The reaction goes to conclusion within 1 to 18 hours.

Then, Compound [VIII] thus obtained is allowed to react with a compound representable by the formula; R¹-Z [wherein R¹ is as defined hereinbefore, and Z stands for halogen (e.g. chlorine, bromine)] in a solvent such as dimethylformamide, dimethylsulfoxide, hexamethylphosphoramide or tetrahydrofuran, solely or as a solvent mixture thereof, in the presence of an inorganic base (e.g. sodium hydroxide, potassium hydroxide, sodium carbonate and potassium carbonate) at a temperature of 10° to 60° C. for 1 to 18 hours to produce Compound [III'] or [V'].

Compound [III''], i.e. Compound [III] wherein X stands for two hydrogen atoms, can be produced by subjecting Compound [III'] to hydrolysis similar to that mentioned hereinbefore.

[B]-Compound [III''], e.e. Compound [III] wherein X is two hydrogen atoms, can be produced by the following process.

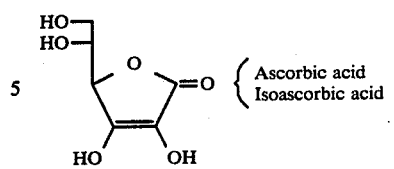
(Ascorbic acid
Isoascorbic acid)

↓ R⁴—Y

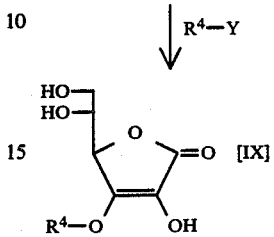
[IX]

↓ R¹—Z

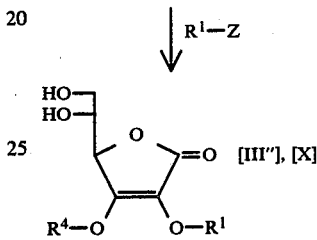
[III''], [X]

In the above method, ascorbic acid or isoascorbic acid is employed as the starting material, and the hydroxyl group of its 3-position is allowed to react, in accordance with the conventional method, with methoxymethyl chloride, ethoxymethyl chloride, benzylbromide, trimethylsilyl chloride, dimethyl tertiary silyl chloride, etc. to give a 3-O-ether compound [IX], then, thus obtained compound [IX] is allowed to react with a compound representable by the formula; R¹-Z [wherein R¹ and Z are as defined hereinbefore] within the temperature range of about 10°~60° C. for about 1 to 20 hours in dimethylformamide, dimethylsulfoxide, hexamethyl phosphoramide, tetrahydrofuran, dioxane, etc., either singly or as a solvent mixture, in the presence of an inorganic base (e.g. potassium carbonate, sodium carbonate, etc.) to give Compound [X].

[C]- Method for producing Compound [V'], i.e. Compound [V] wherein R⁶ stands for O=S< group:

The above compound is produced by allowing thionyl chloride to react with Compound [X].

The reaction is carried out in a solvent, for example tetrahydrofuran, dimethylformamide, methylene chloride, etc. in the presence of an organic base, for example, triethylamine, pyridine, 1,8-diazabicyclo[5,4,0]-7-undecene. The reaction is conducted at about 0°~30° C. for about 1~6 hours. Compounds [III] and [V] as produced in accordance with the afore-mentioned methods are useful as intermediates for the synthesis of, for example, Compound [I].

The compound [I], which possesses oxidation inhibitory activity and also exhibits an LD₅₀ value of 0.8 to 10 g/kg when given orally to mice, thus being of low toxicity, can be used as an antioxidant for food.

The utilization of the compound [I] as an antioxidant for food is conducted by forming it into an antioxidant preparation for food containing the compound [I], followed by addition to, or contacting with, a food product.

In processing or formulating into a preparation, for example, the compound [I] may be formed, without being diluted, by per se known methods, or may be formed after being diluted.

In the case of dilution, for example, a carrier (e.g., lactose, starch, etc.) is admixed with the compound [I], and the mixture is formed into powders or granules by per se known methods.

The foods, to which the antioxidant preparation for food according to the present invention is to be added, include, for example, fruit juice, fruits, edible meat products, fishes and shellfishes, and oils and fats (e.g., salad oil, lard oil, etc.).

As the method of using the antioxidant preparation for food accordding to the present invention, when the compound [I], the active ingredient thereof, is soluble in water, there may be mentioned, for example, a method which comprises adding for dissolution the powdered antioxidant preparation for food according to the present invention directly to foods, such as fruit juice, fruits and edible meat products, or a method which comprises dissolving the antioxidant preparation for food according to the present invention in advance in water and adding the resulting solution to fruit juice, fruits or edible meat products or immersing fishes and shellfishes in the said solution.

The antioxidant preparation for food according to the present invention, in cases in which it is used in edible meat products and fishes and shellfishes, can be brought into an aqueous emulsion thereof with use of an emulsifying agent to thereby put into use.

When the compound [I], the active ingredient, is soluble in oil, the antioxidant preparation for food according to the present invention is added directly to oils and fats.

The used amount of the antioxidant preparation for food according to the present invention, as the compound [I], is for example about 0.02 to 0.04% (W/W) in the case of fruit juice and fruits, about 0.02 to 0.08% (W/W) in the case of edible meat products, about 0.02 to 0.08% (W/W) in the case of it being blended into fishes and shellfishes, about 0.1 to 1% (W/W) as the concentration of a solution to be prepared in the case of immersion, and about 0.002 to 0.02% (W/W) in the case of oils and fats.

Further, the compound [I] may be also used as a bleaching beauty agent for cosmetics. The used amount of the present compound [I] in the bleaching beauty agent for cosmetics, as the compound [I], is for example about 0.1 to 1% (W/V) in the case of lotion, and about 0.1 to 1% (W/W) in the case of cream.

Compound [I] and salts thereof show lipid per-oxidation inhibitory action in the experiments in vitro employing a stable radical or brain homogenates, and, in the ischemia-reperfusion model in the heart of rats or the ischemic brain model in rats or the renal failure model in rats due to oxygen free radicals, they show actions of preventing or improving the respective functional disorders, while they show remarkably low toxicity and no side effects. Compound [I] and salts thereof show therapeutic, prophylactic and improving actions against various functional disorders, for example, ischemic heart diseases (arrhythmia, coronary vasospasm, necrosis of cardiac tissue, myocardial infarction, etc.), subarachnoidal hemorrage, ischemic disorders of cerebral tissue (e.g. cerebral infarction, dementia, senile dementia, etc.), ischemic renal disorders, intestinal ischemic (e.g. intestinal ulcer, etc.), thus being useful as preventing and improving agents of functional disorders in the circulatory system. Specific examples of the use as the above preventing and improving agents of functional disorders in the circulatory system include improving agents of circulatory system, improving agents of renal functions, therapeutic agents of stress intestinal ulcer, etc., e.g. agents of anti-arrhythmia, anti-myocardiac infarction, anti-cerebral infarction, preventing senile dementia, therapy and improvement after subarachmoidal hemorrhage. The compounds of this invention are low in toxicity (e.g. in acute toxicity to mice, no test animals were killed by oral administration at a dose of 1000 mg/kg), and Compound [I] can be safely administered orally or non-orally as pharmaceutical compositions [e.g. tablets, capsules (including softcapsules and micro-capsules), liquids, suppositories, injections, preparations for nasal inhalation] prepared by mixing with per se conventional phamacologically acceptable carriers, excipients, diluents, etc. in accordance with per se known methods. While the dosage varies with the subjects administration routes, symptoms, etc., it is usually, when administered to the above-mentioned mammals, about 0.1 mg/kg~50 mg/kg body weight, preferably about 0.5 mg/kg~20 mg/kg body weight 1~3 times a day.

When Compound [I] is administered non-orally, for examples as a suppository, about 5 mg~10 mg/kg in terms of Compound [I], 1~2 times a day. As the injections, it is desirable to use, in terms of Compound [I], about 0.1 mg/kg~5 mg/kg 1~2 times a day.

For preparation of the above-mentioned compositions for oral use, a binding agent (e.g. hydroxypropyl cellulose, hydroxymethylpropylmethylcellulose, macrogol, etc.), a disintegrator (e.g. starch, carboxymethyl cellulose calcium, etc.), an excipient (e.g. lactose, starch, etc.), a lubricant (e.g. magnesium stearate, talc, etc.), etc. may be suitably incorporated.

When a composition of non-oral use, for example, a injectable preparation, an isotonizing agent (e.g. glucose, D-sorbitol, D-mannitol, sodium chloride, etc.), an antiseptic (e.g. benzylalcohol, chlorobulanol, methyl para-hydroxybenzoate, propyl para-hydroxybenzoate, etc.), a buffer (e.g. phosphate buffer, sodium acetate buffer, etc.), etc. may be suitably incorporated.

Figure 1:
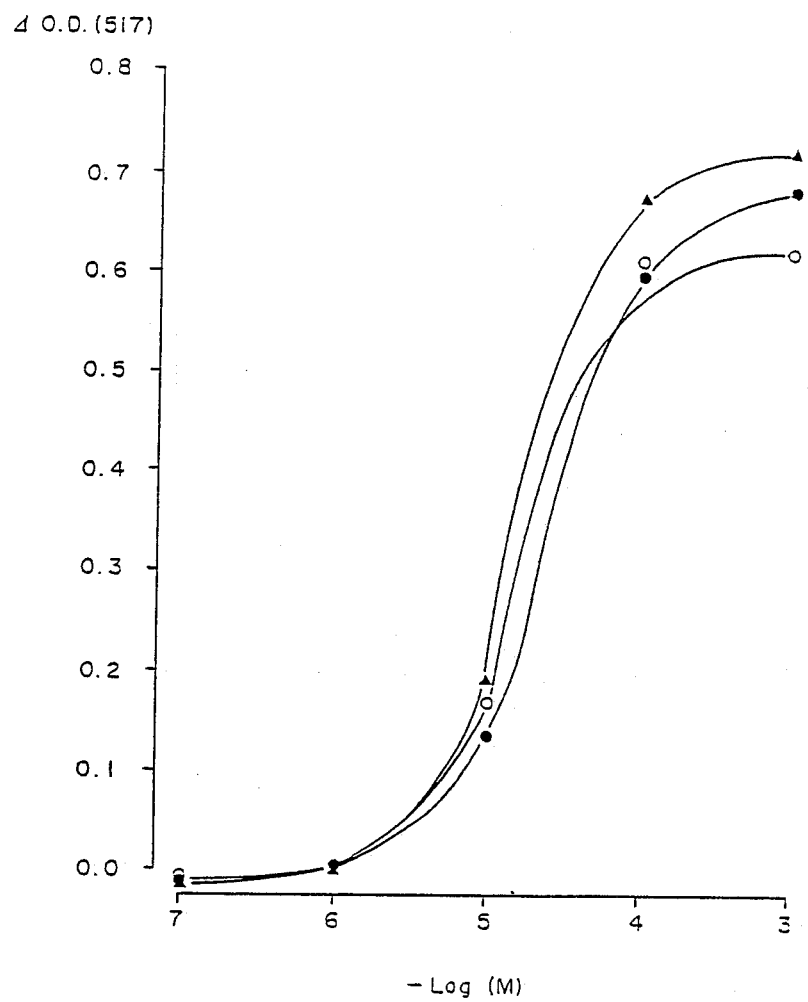
FIG. 1 shows the result of oxidation inhibitory activity disclosed in Experiment 1.

The experiment examples, reference examples and working examples are given below to illustrate the present invention more specifically.

EXPERIMENT 1

Oxidation inhibitory activity determined with the use of a stable radical: In accordance with the method of M. S. Brois [Nature, 181, 1199, 1958], the activity to reduce a stable free radical, $\alpha,\alpha$-diphenyl-$\beta$-picryl hydrazyl (DPPH), was determined, which was used as an index of the oxidation inhibitory activity. More concretely, a test drug [i.e., the compound [I] wherein $R^1 = -(CH_2)_{17}CH_3$, $R^2 = OH$, $R^3 = H$, which is sometimes referred to as "compound (1-12)"] was added to 3 ml of 0.1 mM DDPH ethanol solution. Then, 20 minutes later, the absorbance at a wavelength of 517 nm was measured with the use of a spectrophotometer. The difference in absorbance between a sample solution and reference solvent [not more than 0.5% of DMF] was taken as the reduction activity.

The results of the experiment are shown in FIG. 1, where —●— indicates the results with the above test drug, —○— the results with vitamin E, and —▲— the results with vitamin C.

The above test drug was found to reduce DDPH at the concentration of not less than $10^{-5}$M in a manner dependent upon the amount used. Vitamins C and E showed the activity equal to that of the test drug.

EXPERIMENT 2

Activity to inhibit lipid peroxide formation in rat brain tissue homogenate:

(i) Method:

Male SD rats (12-weeks old) were subjected to exsanguination under anesthesia with pentobarbital, then the brain was excised. The brain tissue was homogenized in a phosphate buffer solution (pH 7.4) to prepare a 5% homogenate. After incubation of the homogenate at 37° C. for 1 hour, the amount of lipid peroxides formed therein was determined by thiobarbituric acid (TBA) method in accordance with the report of Ohkawa et al. on Analytical Biochemistry 95 351, 1979.

The test drug was added to the 5% homogenate before incubation so as to make the final concentration be $10^{-5}$M. The activity to inhibit the formation of lipid peroxides was compared with that of the reference group to which was added the solvent (DMSO), and shown by % inhibition.

(ii) The results are shown in Table 1 below:

The activity to inhibit the formation lipid peroxides varies with the length of the side chain, when the number (n) of the side-chain methylene groups in the general formula [I] was changed in the range of 7-21. When n is in the range of 13-19, the corresponding compounds showed higher activity, reaching 80% or higher in the inhibitory activity, which is more potent than that of vitamin E. As compared with the compound having at the 3-position a methylene chain whose n equals to 17, the compound (1-12) showed higher activity. In the same experimental system, vitamin C rather promoted the formation of lipid peroxides remarkably.

TABLE 1

Activities to inhibit lipid peroxide formation in rat brain tissue homogenates (TBA method)

| Compound [I] | Inhibitory Effect (%) |
|---|---|
| $R^2$ = OH, $R^3$ = H, $R^1$ = —(CH$_2$)$_7$CH$_3$ | −6.6 ± 3.0 |
| $R^2$ = OH, $R^3$ = H, $R^1$ = —(CH$_2$)$_9$CH$_3$ | 40.0 ± 1.1 |
| $R^2$ = OH, $R^3$ = H, $R^1$ = —(CH$_2$)$_{11}$CH$_3$ | 55.7 ± 26.5 |
| $R^2$ = OH, $R^3$ = H, $R^1$ = —(CH$_2$)$_{13}$CH$_3$ | 93.1 ± 5.3 |
| $R^2$ = OH, $R^3$ = H, $R^1$ = —(CH$_2$)$_{14}$CH$_3$ | 100.0 ± 0 |
| $R^2$ = OH, $R^3$ = H, $R^1$ = —(CH$_2$)$_{15}$CH$_3$ | 78.5 ± 11.7 |
| $R^2$ = OH, $R^3$ = H, $R^1$ = —(CH$_2$)$_{17}$CH$_3$ | 88.6 ± 6.8 |
| $R^2$ = OH, $R^3$ = H, $R^1$ = —(CH$_2$)$_{19}$CH$_3$ | 95.4 ± 4.6 |
| $R^2$ = OH, $R^3$ = H, $R^1$ = —(CH$_2$)$_{21}$CH$_3$ | 38.1 ± 16.6 |
| Compounds having a group at the 3-position* | 45.4 ± 8.7 |
| Vitamin C | −71.6 ± 36.8 |
| Vitamin E | 44.9 ± 11.7 |

(Note)
The concentration of each compound is $10^{-5}$ M, and the number of experimental examples of each compound is 3. Inhibitory effects (%) are shown by mean values ± standard error.
(Note) Compounds having a group at the 3-position:

```
   HO
   HO      O
      \   //
       \ =O
       /
      /  \
CH₃(CH₂)₁₇O   OH
```

EXPERIMENT 3

Effects to alleviate renal disorders in rats due to $Fe^{3+}$ nitrilotriacetate:

(i) Method

Male SLC-Wistar rats (4-weeks old, 64~85 g) were used. The animals were housed individually in metabolism cages and allowed free access to feed and water. Body weight, volume of urine and protein in urine (BIO-RAD method) were determined every day, and occult blood reaction was also examined (Labstick method). On the last day of the experiment, the kidney was excised and weighed.

The animals were orally administered once daily with test drugs or vehicles thereof (suspension in gum arabic), and, 40~60 minutes later, were injected intraperitoneally with nitrilotriacetate (NTA) or $Fe^{3+}$-NTA. $Fe^{3+}$-NTA was used in a form of mixture (1:4, molar ratio), and the dosages were 5 mg/kg in terms of $Fe^{3+}$ for 3 days and successively 10 mg/kg for 5 days.

Test drugs were compound (1-12), vitamin C and vitamin E, and the dosages were all 30 mg/kg.

(ii) Results

The results observed on the last day of the experiment are shown in the following Tables 2 and 3.

In the animal groups administered with the vehicle, renal disorders due to $Fe^{3+}$-NTA were observed, and the weight of kidney remarkably increased and, in most of the animals, occult blood test was positive, and remarkable increases in urine volume and protein in urine were observed. In the groups administered with compound (1-12), renal disorders were alleviated, thus, as compared with the groups administered with vehicle, the weight of kidney was significantly less, and the urine volume and urinary protein were significatly less and, only in half of the test animals, occult blood was detected. Vitamin E showed substantially the same effects, but, in more than half of the test animals, occult blood test was positive. Vitamin C did not show significant effect for alleviating renal disorders.

TABLE 2

Effects on renal disorders due to $Fe^{3+}$-nitrilotriacetate (NTA)

| Group | n | Body Weight (g) | Kidney Weight (mg) | Occult Blood Test |
|---|---|---|---|---|
| None*[1] | 2 | 118 | 51 | 0/2 |
| Vehicle*[2] | 6 | 86.6 ± 3.7 | 68.2 ± 2.1 | 5/6 |
| Compound (1-12) | 6 | 95.5 ± 3.0 | 56.5 ± 2.0** | 3/6 |
| Vitamin C | 6 | 89.2 ± 4.1 | 64.5 ± 1.7 | 5/6 |
| Vitamin E | 6 | 99.3 ± 2.3 | 54.3 ± 2.7** | 4/6 |

Dosage of each test drug was 30 mg/kg, orally.
n: number of test animals
*[1]None: Control animals not administered with $Fe^{3+}$-NTA
*[2]Vehicle: Gum arabic suspension

TABLE 3

Effects on renal disorders due to $Fe^{3+}$-nitrilotriacetate (NTA)

| Group | n | Volume of urine (ml/day) | Protein in urine (mg/day) |
|---|---|---|---|
| None | 6 | 5.4 ± 1.2 | 3.0 ± 1.1 |
| Vehicle | 6 | 13.2 ± 2.0 | 15.1 ± 1.9 |
| Compound (1-12) | 6 | 7.4 ± 1.3* | 8.1 ± 2.1* |
| Vitamin C | 6 | 10.3 ± 1.7 | 10.7 ± 2.4 |
| Vitamin E | 6 | 9.0 ± 1.0 | 6.3 ± 1.4* |

Dosage of each test drug was 30 mg/kg, orally.
n: number of test animals
None: Control animals not administered with $Fe^{3+}$-NTA
Vehicle: Gum arabic suspension

EXPERIMENT 4 significant effects were observed by oral administration of vitamin C or E at the dosage of 50 mg/kg.

TABLE 4

Effects on ventricular arrhythmias observed when reperfusion was permitted after closure of the coronary artery in rat hearts

| Group | Ventricular fibrillation | | Ventricular tachycardia | | Extrasystole | Mortality |
|---|---|---|---|---|---|---|
| | Incidence | Duration | Incidence | Duration | | |
| Control | 7/8 (88) | 83.9 ± 27.5 | 7/8 (88) | 31.8 ± 15.0 | 10.8 ± 3.5 | 2/8 (25) |
| Compound (1-12) | | | | | | |
| 50 mg/kg | 2/9* (22) | 1.2 ± 0.8** | 2/9* (22) | 3.2 ± 2.6* | 1.1 ± 0.3** | 0/9 (0) |
| Control | 16/18 (89) | 74.2 ± 30.8 | 17/18 (94) | 26.5 ± 6.8 | 11.8 ± 4.0 | 2/18 (11) |
| Compound (1-12) | | | | | | |
| 20 mg/kg | 9/17* (53) | 31.0 ± 28.2 | 11/17 (65) | 10.2 ± 3.2* | 3.3 ± 0.8** | 1/17 (6) |
| Control | 17/18 (94) | 74.1 ± 36.0 | 17/18 (94) | 16.6 ± 4.4 | 7.3 ± 1.7 | 3/18 (17) |
| Vitamin C | | | | | | |
| 50 mg/kg | 6/6 (100) | 9.7 ± 2.5 | 6/6 (100) | 19.0 ± 3.0 | 5.1 ± 1.0 | 0/6 (0) |
| Vitamin E | | | | | | |
| 50 mg/kg | 6/10 (60) | 43.4 ± 36.0 | 7/10 (70) | 22.3 ± 9.7 | 7.0 ± 4.1 | 1/10 (10) |

*: $p < 0.05$, **: $p < 0.01$, as compared with Control Group

Action to inhibit ventricular arrhythmias occurred during coronary artery occlusion-reperfusion in rat hearts (i) Method Male SD rats (9~13 - weeks old, 250~370 g) were used. The animals were subjected to thoractonomy under artificial respiration while anesthesia was maintained by administering pentobarbital. The left anterior descending coronary artery was ligated with silk thread for 5 minutes, then the ligation was released to allow reperfusion, and animals were observed for 10 minutes. By recording standard limb lead II electrocardiograms, occurrence of ventricular arrhythmias was examined.

The animals were administered, under non-anesthesia, with test drugs as a gum arabic suspension at the dosage of 30 mg/kg at the time of about 90 minutes and of 20 mg/kg at the time of about 45 minutes (total: 50 mg/kg), or at the dosage of 10 mg/kg each (total: 20 mg/kg) at the time of about 90 minutes and about 45 minutes prior to closure of the coronary artery. The results are shown in Table 4 in terms of the total amount of the dosage.

(ii) Results

When reperfusion was permitted after the closure for 5 minutes of the left anterior descending coronary artery, ventricular arrhythmias, typically exemplified by occasionally occurring premature ventricular contractions (PVCs), ventricular tachycardia (VT) and ventricular fibrillation (VF), were observed. VT and VF were paroxysmally repeated, or sustained VF resulted in death.

In the group administered with the vehicle, VF and VT were observed in more than 90% of the animals, and the durations were respectively about 80 and 20~30 seconds. Among the animals, 10~25% were killed by occurrence of sustained VF.

In the groups administered with 20 and 50 mg/kg each of compound (1-12), occurrence of those arrhythmias was suppressed significantly and depending on the dosages. Even when the arrhythmias occurred, the period of time during which the symptom lasted was shortened. Consequently the mortality due to VF was low. Frequency of occasional PVCs was around 10 times/minutes in the groups of the vehicle, while, in the group administered with compound (1-12), the frequency was less significantly. On the other hand, no Incidences of ventricular fibrillation and ventricular tachycardia are shown by the percentage of the number of animals presenting the symptoms relative to the number of animals subjected to the test, and the duration of the symptoms was shown in average ±SEM by seconds. Extrasystole is shown by the number of systole/-min, and the mortality is shown by the percentage of the number of animals killed relative to the number of animals subjected to the test.

EXPERIMENT 5

Inhibition of ischemic seizure due to ligation of bilateral common carotid arteries in SHR rats (i) Method Male SHR rats (22-weeks old, about 360 g) were used. Under light anesthesia with ether, the animals were subjected to midline incision at the neck and the bilateral common carotid arteries were singled, then ligated to cause cerebral ischemia. Thereafter, the animals were allowed to awake from the anesthesia, and the behavior was observed for about 4 hours. The animals were orally administered with test drugs as a gum arabic suspension 60 minutes before the ligation of the bilateral common carotid arteries. The results are shown in Table 5.

(ii) Results

When the bilateral common carotid arteries were ligated to cause cerebral ischemia, convulsion, an ischemic seizure, was observed after about 150 minutes in the vehicle group. The seizure was observed in about 90% of the rats within 180 minutes. But, in the group orally administered with compound (1-12) at a dosage of 100 mg/kg, the appearance of the convulsion was significantly delayed by about 40 minutes. The incidence of appearance of the seizure within 180 minutes was significantly inhibited to 20%.

TABLE 5

Activity to inhibit ischemic convulsive seizure observed when bilateral common carotid arteries were ligated in SHR rats

| Group | n | Ischemic convulsive seizure | |
|---|---|---|---|
| | | Time (min) | Incidence[a] |
| Vehicle | 41 | 151 ± 4 | 36/41 (87.8%) |

TABLE 5-continued

Activity to inhibit ischemic convulsive seizure observed when bilateral common carotid arteries were ligated in SHR rats

| Group | n | Ischemic convulsive seizure | |
|---|---|---|---|
| | | Time (min) | Incidence[@] |
| Compound (1-12) | 5 | 199 | 13* | 1/5* (20%) |

Compound (1-12): 100 mg/kg p.o.; Vehicle: Gum arabic suspension
[@]: Within 180 minutes
*: $P < 0.05$

EXPERIMENT 6

Acute toxicity in mice (i) Method

Male Crj-ICR mice (4-weeks old, 21~26 g) were used. The animals, divided into groups, each consisting of six mice, were administered orally with compound (1-12) at the dosage of 300 or 1000 mg/kg. Then, each group was housed in a cage, and observed for 24 hours. The test drugs were suspended in gum arabic, and administered at the volume of 0.1 ml/10 g.

(ii) Results

In both groups administered with compound (1-12) at the dosages of 300 and 1000 mg/kg, the state of sedation and ptosis were observed, but both were recovered within 3 hours. During 24-hour-observation, no test animals of either group were killed.

EXPERIMENT 7

Sardine, after having removed the internals and bones, was minced, and the mince meat was formed without addition of, and with addition at a rate of 0.03% and 0.05% of, the compound [I'] wherein $R_1=(CH_2)_4CH_3$ to prepare meatballs. The meatballs were preserved by freezing at $-20°$ C., and the peroxide value (POV) was measured with relation to a length of time elapsed. The results are shown in Table below.

TABLE

| Added amount | No. of days preserved | | | |
|---|---|---|---|---|
| | 0 | 30 | 60 | 90 |
| — | 6.9 | 34.5 | 54.1 | 70.3 |
| 0.03% | 6.9 | 10.3 | 15.6 | 30.5 |
| 0.05% | 6.9 | 7.5 | 10.4 | 28.7 |

EXPERIMENT 8

In a Petri dish of a diameter of about 10 cm was placed 25 g of salad oil, which was preserved in a thermostat at 60° C. without addition of, and with addition for dissolution at a rate of 0.03% and 0.05% of, the compound [I'] wherein $R_1=(CH_2)_{16}CH_3$, and the peroxide value (POV) was measured with relation to a length of time elapsed. The results are shown in Table below.

TABLE

| Added amount | No. of days preserved | | | |
|---|---|---|---|---|
| | 0 | 30 | 60 | 90 |
| — | 2.3 | 10 | 57 | 83 |
| 0.03% | 2.3 | 5 | 34 | 51 |
| 0.05% | 2.3 | 4 | 29 | 45 |

REFERENCE EXAMPLE 1

(1) L-Ascorbic acid acetonide (42 g, 0.19 mole) was dissolved in a solvent mixture of dimethylformamide (100 ml) and hexamethylphosphoramide (100 ml), and potassium carbonate (32 g, 0.23 mole) was added to the solution, followed by ice-cooling. A solution of chloromethyl methyl ether (18 g, 0.22 mole) in tetrahydrofuran (25 ml) was added dropwise to the mixture over the 20 minutes period. After stirring at room temperature for 2.5 hours, water (200 ml) was added to the reaction mixture, to which 2N hydrochloric acid was added to adjust to pH 5.0, followed by extraction with four portions of ethyl acetate. The organic layer was washed with water, dried and then concentrated under reduced pressure, and the residue was subjected to silica gel column chromatography, followed by elution with isopropyl ether - ethyl acetate (2:1). The eluate was concentrated, and the residue was recrystallized from the same solvent system to give L-5, 6-O,O-isopropylidene-3-O-methoxymethylascorbic acid (46 g). m.p. 93°14 94° C.

Elemental analysis, for $C_{11}H_{16}O_7$

| Found: | C, 50.84; | H, 6.05% |
|---|---|---|
| Calcd.: | C, 50.77; | H, 6.20 |

(2) L-b 5,6-O,O-Isopropylidene-3-O-methoxymethylascorbic acid (1.84 g, 7.1 mmole) was dissolved in dimethylsulfoxide (10 ml), and octadecyl iodide (2.68 g) and potassium carbonate (1.0 g) were added to the solution, followed by allowing the reaction to proceed at 60° C. for 6 hours. After the conclusion of the reaction, water (50 ml) was added to the reaction mixture, followed by extraction of the reaction product with ethyl acetate. The organic layer was washed with water, dried and concentrated under reduced pressure, and the residue was subjected to silica gel column chromatography, followed by elution with isopropyl ether. The eluate was concentrated, and the residue was recrystallized from isopropyl ether - ethyl acetate to give L-5,6-O,O-isopropylidene-3-O-methoxymethyl-2-O-octadecylascrobic acid (R1-11) (0.8 g). The physicochemical properties are shown in Table 6.

By the same procedure as in Reference Example 1, compounds shown in Table 6 [(R1-1) to (R1-33)] were prepared.

(5- and 6-positions form a isopropylidene)

TABLE 6

| Compound | $R^1$ | NMR |
|---|---|---|
| | m.p. (°C.) | |
| R1-1 | —(CH$_2$)$_5$Me<br>Oil | 0.87(3H, m), 1.25(8H, m), 1.34(3H, s), 1.37(3H, s), 3.50(3H, s), 4.09(5H, m), 4.51(1H, d, 2Hz), 5.40(2H, s) |
| R1-2 | —(CH$_2$)$_7$Me<br>Oil | 0.85(3H, m), 1.25(12H, s), 1.34(3H, s), 1.37(3H, s), 3.46(3H, s), 4.12(5H, m), 4.56(1H, d, 2Hz), 5.46(2H, s) |
| R1-3 | —(CH$_2$)$_8$Me<br>Oil | 0.85(3H, m), 1.27(14H, m), 1.33(3H, s), 1.36(3H, s), 3.48(3H, s), 4.12(5H, m), 4.57(1H, d, 2Hz), 5.45(2H, s) |
| R1-4 | —(CH$_2$)$_{10}$Me<br>Oil | 0.87(3H, m), 1.26(18H, m), 1.33(3H, s), 1.37(3H, s), 3.48(3H, s), 4.12(5H, m), 4.56(1H, d, 2Hz), 5.46(2H, s) |
| R1-5 | —(CH$_2$)$_{11}$Me<br>Oil | 0.85(3H, m), 1.25(20H, m), 1.34(3H, s), 1.37(3H, s), 3.47(3H, s), 4.12(5H, m), 4.55(1H, d, 2Hz), 5.46(2H, s) |
| R1-6 | —(CH$_2$)$_{12}$Me<br>Oil | 0.86(3H, m), 1.25(22H, m), 1.34(3H, s), 1.37(3H, s), 3.48(3H, s), 4.13(5H, m), 4.56(1H, d, 2Hz), 5.45(2H, s) |
| R1-7 | —(CH$_2$)$_{13}$Me<br>Oil | 0.86(3H, m), 1.25(24H, m), 1.33(3H, s), 1.37(3H, s), 3.45(3H, s), 4.12(5H, m), 4.56(1H, d, 2Hz), 5.46(2H, s) |
| R1-8 | —(CH$_2$)$_{14}$Me<br>Oil | 0.87(3H, m), 1.24(26H, m), 1.33(3H, m), 1.37(3H, s), 3.49(3H, s), 4.43(5H, m), 4.56(1H, d, 2Hz), 5.44(2H, s) |
| R1-9 | —(CH$_2$)$_{15}$Me<br>44–45 | 0.87(3H, m), 1.25(28H, m), 1.34(3H, s), 1.38(3H, s), 3.50(3H, s), 4.11(5H, m), 4.56(1H, d, 2Hz), 5.44(2H, s) |
| R1-10 | —(CH$_2$)$_{16}$Me<br>Oil | 0.85(3H, m), 1.26(30H, m), 1.33(3H, s), 1.36(3H, s), 3.47(3H, s), 4.11(5H, m), 4.57(1H, d, 2Hz), 5.47(2H, s) |
| R1-11 | —(CH$_2$)$_{17}$Me<br>50–52 | 0.85(3H, m), 1.25(32H, m), 1.33(3H, s), 1.37(3H, s), 3.50(3H, m), 4.12(5H, m), 4.57(1H, d, 2Hz), 5.47(2H, s) |
| R1-12 | —(CH$_2$)$_{19}$Me<br>57–58 | 0.85(3H, m), 1.25(36H, m), 1.33(3H, s), 1.36(3H, s), 3.47(3H, s), 4.25(5H, m), 4.57(1H, d, 2Hz), 5.43(3H, s) |
| R1-13 | —(CH$_2$)$_{10}$COOMe<br>Oil | 1.29(16H, m), 2.30(2H, t, 7Hz), 3.51(3H, s), 3.66(3H, s), 4.11(3H, m), 4.57(1H, d, 2Hz), 5.45(2H, s) |
| | properties | |
| R1-14 | —(CH$_2$)$_9$OH<br>Oil | 1.30(20H, m), 3.50(3H, s), 3.51(3H, m), 4.03(5H, m), 4.51(1H, d, 2Hz), 5.58(2H, s) |
| R1-15 | —Bz<br>Oil | 1.34(3H, s), 1.37(3H, s), 3.38(3H, s), 4.06(3H, m), 4.50(1H, d, 2Hz), 5.05(2H, s), 5.17(2H, s), 7.20(5H, s) |
| R1-16 | —(CH$_2$)$_3$Ph<br>Oil | 1.31(3H, s), 1.35(3H, s), 1.97(2H, m), 2.67(2H, m), 3.42(3H, s), 4.06(5H, m), 4.50(1H, d, 2Hz), 5.36(2H, s), 7.16(5H, m) |
| R1-17 | 4-Br—Bz<br>Oil | 1.34(3H, s), 1.37(3H, s), 3.46(3H, s), 4.12(3H, m), 4.58(1H, d, 2Hz), 5.09(2H, s), 5.32(2H, s), 7.31(2H, d, 7Hz), 7.50(2H, d, 7Hz) |
| R1-18 | 4-Cl—Bz<br>Oil | 1.34(3H, s), 1.38(3H, s), 3.46(3H, s), 4.14(3H, m), 4.56(1H, d, 2Hz), 5.10(2H, s), 5.31(2H, s), 7.30(4H, s) |
| R1-19 | 4-Me—Bz<br>Oil | 1.34(3H, s), 1.39(3H, s), 2.33(3H, s), 3.43(3H, s), 4.10(3H, m), 4.56(1H, d, 2Hz), 5.10(2H, s), 5.26(2H, m), 7.16(2H, d, 8Hz), 7.31(2H, d, 8Hz) |
| R1-20 | 3-Me—Bz<br>Oil | 1.34(3H, s), 1.38(3H, s), 2.34(3H, s), 3.43(3H, s), 4.11(3H, m), 4.54(1H, d, 2Hz), 5.24(2H, s), 5.24(2H, m), 7.20(4H, m) |
| R1-21 | 4-iPr—Bz<br>Oil | 1.23(6H, d, 7Hz), 2.90(1H, hep, 7Hz), 3.42(3H, s), 4.12(3H, m), 4.56(1H, d, 2Hz), 5.10(2H, s), 5.25(2H, m), 7.29(4H, m) |
| R1-22 | 4-COOMe—Bz<br>Oil | 1.33(3H, s), 1.37(3H, s), 3.46(3H, s), 3.90(3H, s), 4.12(3H, m), 4.57(1H, d, 2Hz), 5.19(2H, s), 5.32(2H, s), 7.49(2H, d, 8Hz), 8.04(2H, d, 8Hz) |
| R1-23 | 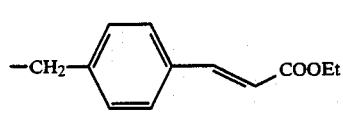Oil | 1.32(3H, t, 7Hz), 1.33(3H, s), 1.37(3H, s), 3.44(3H, s), 4.10(3H, m), 4.23(2H, q, 7Hz), 4.57(1H, d, 2Hz), 5.14(2H, s), 5.31(2H, s), 6.42(1H, d, 16Hz), 7.47(4H, m), 7.67(1H, d, 16Hz) |

TABLE 6-continued

| Compound | R¹ | NMR |
|---|---|---|
| R1-24 | —CH₂CH(Ph)₂<br>Oil | 1.32(6H, s), 2.46(2H, m), 3.44(3H, s), 4.06(6H, m), 4.53(1H, d, 2Hz), 5.36(2H, s), 7.25(10H, s) |
| R1-25 | —(CH₂)₈OBz<br>Oil | 1.34(12H, m), 1.37(6H, s), 3.46(2H, t, 7Hz), 3.49(3H, s), 4.09(5H, m), 4.48(2H, s), 4.54(1H, d, 2Hz), 5.42(2H, s), 7.31(5H, s) |
| R1-26 | —CH₂-Cyclohexyl<br>Oil | 1.34(3H, s), 1.38(3H, s), 1.50(11H, m), 3.50(3H, s), 4.12(5H, m), 4.56(1H, d, 2Hz), 5.43(2H, s) |
| R1-27 | -Phenacyl<br>Oil | 1.33(3H, s), 1.37(3H, s), 3.53(3H, s), 4.11(3H, m), 4.61(1H, d, 2Hz), 5.54(2H, m), 5.74(2H, m), 7.53(3H, m), 7.91(2H, m) |
| R1-28 | 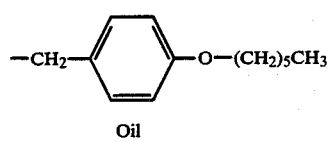<br>Oil | 0.88(3H, m), 1.35(14H, m), 3.40(3H, s), 3.91(3H, t, 7Hz), 4.08(3H, m), 4.52(1H, d, 2Hz), 5.01(2H, s), 5.18(2H, s), 6.80(2H, d, 7Hz), 7.27(2H, d, 7Hz) |
| R1-29 | 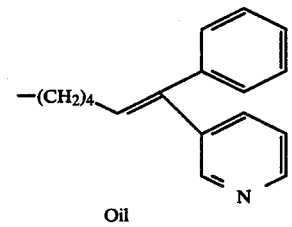<br>Oil | 1.36(3H, s), 1.38(3H, s), 1.66(6H, m), 2.18(2H, m), 3.48(3H, s), 4.18(7H, m), 4.55(1H, m), 5.40(2H, s), 6.11(1H, t), 7.38(7H, m), 8.42(1H, m), 8.50(1H, m) |
| R1-30 | 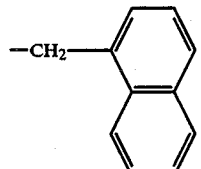<br>Oil | 1.36(3H, s), 1.44(3H, s), 3.36(3H, s), 3.07(3H, m), 4.51(1H, d), 5.08(2H, s), 5.57(2H, s), 7.45(7H, m) |
| R1-31 | 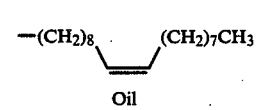<br>Oil | 0.88(3H, m), 1.30(22H, m), 1.36(3H, s), 1.37(3H, s), 2.00(4H, m), 3.51(3H, m), 4.10(5H, m), 4.57(1H, d), 5.31(2H, m), 5.42(2H, s) |
| R1-32 | —CH₂COOMe<br>Oil | 1.37(6H, s), 3.52(3H, s), 3.74(3H, s), 4.12(3H, m), 4.54(1H, d), 4.75(2H, s), 5.49(1H, d), 5.62(1H, d) |
| R1-33 | —(CH₂)₄COOMe<br>Oil | 1.37(6H, s), 1.72(4H, m), 2.35(2H, m), 3.49(3H, s), 3.65(3H, s), 4.10(5H, m), 5.36(2H, s) |

Bz: benzyl, Me: methyl, Ph: phenyl, iPr: isopropyl, Et: ethyl

REFERENCE EXAMPLE 2

(1) L-ascorbic acid acetonide (21.6 g, 0.1 mole) was dissolved in dimethylformamide (120 ml), and the solution was cooled with ice. To the solution were added potassium carbonate (14 g, 0.1 ml) and successively benzyl bromide (11.2 ml), followed by stirring at room temperature for 20 hours. After the conclusion of the reaction, water (100 ml) was added to the reaction solution. To the mixture was added 2N hydrochloric acid to adjust to pH 5.0, followed by extraction with two portions of ethyl acetate. The organic layer was washed with water, dried (over magnesium sulfate) and then concentrated under reduced pressure. The product was subjected to silica gel column chromatography, and elution was effected with isopropyl ether - ethyl acetate (3:1). The eluate was concentrated, and then the residue was recrystallized from isopropyl ether - ethyl acetate to give L-5,6-O,O-isopropylidene-3-O-benzylascorbic acid (13 g, 40%), m.p. 105°–106° C.

(2) L-5,6-O,O-isopropylidene-3-O-benzylascorbic acid (3.06 g, 0.01 mole) was dissolved in a solvent mixture of dimethyl-sulfoxide (20 ml) and tetrahydrofuran (15 ml), and potassium carbonate (1.5 g, 0.011 mole) was added to the solution. Then, octadecyl iodide (3.83 g) was added to the mixture, followed by stirring at room temperature for 18 hours. After the conclusion of the reaction, water (100 ml) was added to the reaction mixture, followed by extraction with ethyl acetate. The organic layer was washed with water, dried (over magnesium sulfate) and then concentrated under reduced pressure. The residue was subjected to silica-gel column chromatography, followed by elution with isopropyl ether - ethyl acetate (10:1) to give L-5,6-O,O-isopropylidene-3-O-benzyl-2-O-octadecyl-ascorbic acid [compound (R2-7)] (3.8 g). The physico-chemical properties are shown in Table 7.

By the same procedure as in Reference Example 2, compounds shown in Table 7 [(R2-1) to (R2-12)] were prepared.

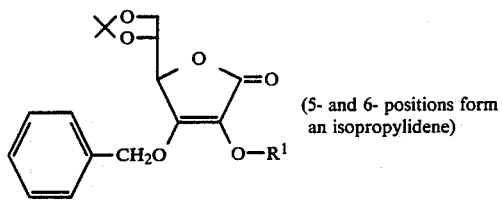
(5- and 6- positions form an isopropylidene)

solution, followed by stirring at 50° C. for 24 hours. After the conclusion of the reaction, the reaction solution was concentrated under reduced pressure, and the reaction product was extracted with ethyl acetate. The organic layer was washed with water, dried and then concentrated under reduced pressure, and the residue was recrystallized from isopropyl ether - ethyl acetate to give 3-O-benzyl-2-O-octadecylascorbic acid [compound (R 3-7)](2.6 g).

The physico-chemical properties are shown in Table 8.

(2) The compounds obtained in Reference Example 2 were processed by a procedure analogous to the above to prepare compounds [(R 3-1) to (R3-12)], which are shown in Table 8.

TABLE 7

| Compound | $R^1$ m.p. (°C.) | NMR |
|---|---|---|
| R 2-1 | —$(CH_2)_7$Me<br>Oil | 0.87(3H, m), 1.27(12H, m), 1.34(3H, s), 1.37(3H, s), 4.06, (5H, m), 4.54(1H, d, 2Hz), 5.46(2H, s), 7.36(5H, s) |
| R 2-2 | —$(CH_2)_9$Me<br>Oil | 0.86(3H, m), 1.26(16H, m), 1.34(3H, s), 1.37(3H, s), 4.08(5H, m), 4.54(1H, d, 2Hz), 5.46(2H, s), 7.37(5H, s) |
| R 2-3 | —$(CH_2)_{13}$Me<br>Oil | 0.86(3H, m), 1.24(26H, m), 1.34(3H, s), 1.37(3H, s), 4.08(5H, m), 4.53(1H, d, 2Hz), 5.46(2H, s), 7.36(5H, s) |
| R 2-4 | —$(CH_2)_{14}$Me<br>Oil | 0.86(3H, m), 1.26(26H, m), 1.34(3H, s), 1.37(3H, s), 4.10(5H, m), 4.53(1H, d, 2Hz), 5.46(2H, s), 7.36(5H, s) |
| R 2-5 | —$(CH_2)_{15}$Me<br>Oil | 0.85(3H, m), 1.25(26H, m), 1.34(3H, s), 1.37(3H, s), 4.06(5H, m), 4.54(1H, d, 2Hz), 5.46(2H, s), 7.37(5H, s) |
| R 2-6 | —$(CH_2)_{16}$Me<br>Oil | 0.87(3H, m), 1.25(28H, m), 1.34(3H, s), 1.37(3H, s), 4.08(5H, m), 4.54(1H, d, 2Hz), 5.46(2H, s), 7.36(5H, s) |
| R 2-7 | —$(CH_2)_{17}$Me<br>44–45 | 0.88(3H, m), 1.26(32H, m), 1.38(6H, s), 4.08(5H, m), 4.51(1H, d, 2Hz), 5.43(2H, s), 7.29(5H, s) |
| R 2-8 | —$(CH_2)_{19}$Me<br>48–50 | 0.87(3H, m), 1.24(36H, m), 1.34(3H, s), 1.37(3H, s), 4.06(5H, m), 4.54(1H, d, 2Hz), 5.46(2H, s), 7.36(5H, s) |
| R 2-9 | —$(CH_2)_{21}$Me<br>60–61 | 0.87(3H, m), 1.24(40H, m), 1.34(3H, s), 1.37(3H, s), 4.08(5H, m), 4.53(1H, d, 2Hz), 5.45(2H, s), 7.36(5H, s) |
| R 2-10 | —$(CH_2)_{10}$-[tetrasubstituted benzene with OBz, OMe, Me, OMe, OBz]<br>Oil | 1.26(16H, m), 1.35(3H, s), 1.37(3H, s), 2.14(3H, s), 4.12(3H, m), 4.51(1H, m), 4.81(2H, m), 4.88(2H, s), 4.95(2H, s), 7.30(15 Hz), |
| R 2-11 | —$CH_2CON$(morpholino)<br>Oil | 1.37(6H, s), 3.65(8H, m), 4.10(3H, m), 4.55(2H, m), 4.81(2H, m), 5.67(2H, s), 7.30(5H, s) |
| R 2-12 | —$CH_2CON$(2-COOMe-piperidino)<br>Oil | 1.32(3H, s), 1.36(3H, s), 2.04(3H, m), 3.60(3H, s), 4.02(3H, m), 4.23(3H, m), 4.53(3H, m), 7.34(5H, m) |

REFERENCE EXAMPLE 3

(1) L-5,6-O,O-Isopropylidene-3-O-benzyl-2-O-octadecylascorbic acid (3.8 g) was dissolved in a solvent mixture of tetrahydrofuran (40 ml) and methanol (10 ml), and 2N hydrochloric acid (20 ml) was added to the

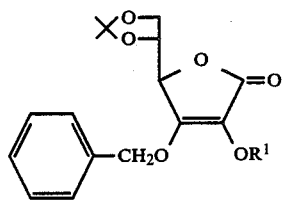

TABLE 8

| Compound | R$^1$ m.p. (°C.) | NMR |
|---|---|---|
| R 3-1 | —(CH$_2$)$_7$Me<br>Oil | 0.87(3H, m), 1.26(12H, m), 4.00(5H, m), 4.66(1H, d, 2Hz), 5.45(2H, s), 7.32(5H, s) |
| R 3-2 | —(CH$_2$)$_9$Me<br>Oil | 0.86(3H, m), 1.25(16H, m), 3.80(2H, m), 4.00(3H, m), 4.68(1H, d, 2Hz), 5.46(2H, s), 7.36(5H, s) |
| R 3-3 | —(CH$_2$)$_{13}$Me<br>65–66 | 0.86(3H, m), 1.25(24H, m), 3.80(2H, m), 4.00(3H, m), 4.68(1H, d, 2Hz), 5.47(2H, s), 7.35(5H, s), |
| R 3-4 | —(CH$_2$)$_{14}$Me<br>63–63 | 0.87(3H, m), 1.23(26H, m), 3.82(2H, m), 4.02(3H, m), 4.68(1H, d, 2Hz), 5.47(2H, s), 7.36(5H, s) |
| R 3-5 | —(CH$_2$)$_{15}$Me<br>71–72 | 0.86(3H, m), 1.25(28H, m), 3.85(2H, m), 4.02(3H, m), 4.69(1H, d, 2Hz), 5.47(2H, s), 7.37(5H, s) |
| R 3-6 | —(CH$_2$)$_{16}$Me<br>57–58 | 0.88(3H, m), 1.25(30H, m), 3.79(2H, m), 4.00(3H, m), 4.67(1H, d, 2Hz), 5.44(2H, s), 7.33(5H, s) |
| R 3-7 | —(CH$_2$)$_{17}$Me<br>75–76 | 0.87(3H, m), 1.25(32H, m), 3.80(2H, m), 4.01(3H, m), 4.68(1H, m), 5.46(2H, s), 7.34(5H, s) |
| R 3-8 | —(CH$_2$)$_{19}$Me<br>77–78 | 0.86(3H, m), 1.24(36H, m), 4.00(5H, m), 4.68(1H, m), 5.46(2H, s), 7.36(5H; s), |
| R 3-9 | —(CH$_2$)$_{21}$Me<br>83–85 | 0.86(3H, m), 1.25(40H, m), 3.82(2H, m), 4.02(3H, m), 4.69(1H, d, 2Hz), 5.46(2H, s), 7.36(5H, s) |
| R 3-10 | —(CH$_2$)$_{10}$—[substituted benzene with OBz, OMe, OMe, OMe, OMe, OBz]<br>Oil | 1.40(16H, m), 2.13(3H, m), 2.23(2H, m), 3.91(6H, s), 4.06(5H, m), 4.90(2H, s), 4.97(2H, m), 5.57(2H, m), 7.30(15H, m) |
| R 3-11 | —CH$_2$CON(morpholine)<br>Oil | 3.37(4H, m), 3.49(4H, m), 3.90(2H, m), 4.20(1H, m), 4.79(2H, m), 4.89(1H, d), 5.56(1H, d), 5.75(1H, d), 7.40(5H, s) |
| R 3-12 | —CH$_2$CON(piperidine-COOMe)<br>Oil | 2.04(4H, m), 3.49(2H, m), 3.60(3H, s), 4.02(3H, m), 4.23(1H, m), 4.53(3H, m), 7.34(5H, s) |

REFERENCE EXAMPLE 4

L-5,6-O,O-Isoprpylidene ascorbic acid (52 g, 0.24 mole) was dissolved in a mixture of tetrahydrofuran (200 ml) and DMF(50 ml). Potassium carbonate (42 g, 0.3 mole) was added to the reaction mixture and the mixture was stirred for 10 minutes at room temperature. To the reaction mixture chloromethy ethyl ether (27 ml, 0.3 mole) was added during 5 minutes under keeping about 20° C. in an ice bath. After stirring for 4 hours at room temperature, the reaction mixture was poured onto water (300 ml), adjusted at pH 8 by adding 2N hydrochloric acid and then extracted twice (400 ml, 200 ml) with ethyl acetate. The organic layer was washed with water, dried and concentrated under reduced pressure. The resulting crude product was purified with silica gel column chromatography (300 g, Merck Ltd. Art 7734, developing solvent; ethyl acetate:isopropyl ether=1:2) and then recrystallized from isopropyl ether (crystallized out in refrigerator) to give 5,6-O,O-isopropylidene-3-O-ethoxymethyl-(L)-ascorbic acid (40 g, 61%).

REFERENCE EXAMPLE 5

L-5,6-O,O-Isopropylidene-3-O-ethoxymethyl ascorbic acid (13.6 g, 0.05 mole) and octadecyl iodide (20 g, 0.055 mole) were dissolved in a mixture of tetrahydrofuran (200 ml) and DMSO (50 ml), and added potassium carbonate (8 g, 0.06 mole) to the reaction mixture under stirring at room temperature. After stirring the mixture for 3 hours at 50° C., water (300 ml) was added to the mixture. The reaction mixture was adjusted to pH 7 with 2N hydrochloric acid and extracted with isopropyl ether (600 ml). The organic layer was washed with water, dried and concentrated under reduced pressure. The resulting crude product was purified with silica gel column chromatography (300 g, developing solvent; isopropyl ether) to give 5,6-O,O-isopropylidene-3-O-ethoxymethy-2-O-octedecyl-(L)-ascorbic acid (15 g, 57%). This compound did not form any crystals at room temperature.

REFERENCE EXAMPLE 6

(1) To a solution of 2-O-octadecyl-L-ascorbic acid (0.8 g, 2 mmole) in chloroform (20 ml) was added pyridine (1 ml), followed by adding dropwise benzoyl chloride (0.28 g, 2 mmole) at room temperature. The reaction mixture was stirred for one hour, to which was added 2N hydrochloric acid to acidify it. The organic layer was washed with water and dried (over magnesium sulfate). The solvent was evaporated off, and the product was recrystallized from isopropyl ether-ethyl acetate to give 3-O-benzoyl-2-O-octadecyl-L-ascorbic acid (0.6 g, 49%), m.p. 68°–69° C. $C_3H_{48}O_7$ (Found: C,69.94; H,8.98%. Anal. Calcd: C,69.89; H,9.08)

(2) By the same procedure as in the above, 2-O-hexadecyl-L-ascorbic acid was subjected to benzoylation to give 3-O-benzoyl-2-O-hexadecyl-L-ascorbic acid, m.p. 77°–78° C. $C_{29}H_{44}O_7$ (Found: C,69.21; H,8.82%. Anal. Calcd.: C,69.02; H,8.79)

EXAMPLE 1

L-5,6-O,O-Isopropylidene-3-O-methoxymethyl-2-O-octadecylascorbic acid (1.2 g) was dissolved in a solvent mixture of methanol (30 ml) and tetrahydrofuran (10 ml), and 2N hydrochloric acid (10 ml) was added to the solution, followed by stirring at 50° C. for 6 hours. The reaction solution was concentrated under reduced pressure, and the reaction product was extracted with ethyl acetate. The organic layer was washed with water, dried (over magnesium sulfate) and then concentrated under reduced pressure, and the residue was recrystallized from isopropyl ether-ethyl acetate to give 2-O-octadecylascorbic acid [compound (1-12)](0.82 g). This compound was also obtained from L-5,6-O,O-isopropylidene-3-O-ethoxymethyl ascorbic acid by hydrolysis mentioned above. The physico-chemical properties are shown in Table 9.

EXAMPLE 2

3-O-Benzyl-2-O-octadecylascorbic acid (2.1 g) was dissolved in ethyl acetate (25 ml), and 5% Pd-C (0.5 g) was added to the solution to conduct catalytic reduction under atmospheric pressure. The catalyst was filtered out, and the filtrate was concentrated under reduced pressure. The reaction product was recrystallized from isopropyl ether-ethyl acetate to give 2-O-octadecylascorbic acid [compound (1-12)](1.5 g).

The physico-chemical properties are shown in Table 9.

EXAMPLE 3

Compounds [(1-1) to (1-38)] prepared by a procedure similar to the above Examples 1 and 2 are set forth in Table 9.

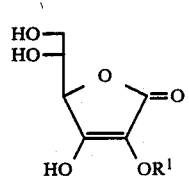

TABLE 9

| Compound | $R^1$ | Ex. No. depended | m.p. (°C.) | NMR |
|---|---|---|---|---|
| 1-1 | $-(CH_2)_5Me$ | 1 | 100–101 | 0.88(3H, m), 1.32(8H, m), 3.54(2H, m), 3.89(3H, m), 4.70(1H, d, 1Hz) |
| 1-2 | $-(CH_2)_7Me$ | 1, 2 | 115–117 | 0.84(3H, m), 1.26(12H, m), 3.53(2H, m), 3.85(3H, m), 4.70(1H, d, 1Hz) |
| 1-3 | $-(CH_2)_8Me$ | 1, 2 | 122–123 | 0.86(3H, m), 1.25(14H, m), 3.54(2H, m), 3.87(3H, m), 4.71(1H, d, 1Hz) |
| 1-4 | $-(CH_2)_9Me$ | 2 | 118–120 | 0.85(3H, m), 1.24(16H, m), 3.43(2H, m), 3.86(3H, m), 4.72(1H, d, 1Hz) |
| 1-5 | $-(CH_2)_{10}Me$ | 1 | 124–125 | 0.86(3H, m), 1.24(18H, m), 3.50(2H, m), 3.87(3H, m), 4.71(1H, d, 1Hz) |
| 1-6 | $-(CH_2)_{11}Me$ | 1 | 127–128 | 0.85(3H, m), 1.24(20H, m), 3.53(2H, m), 3.91(3H, m), 4.72(1H, d, 1Hz) |
| 1-7 | $-(CH_2)_{12}Me$ | 1 | 129–130 | 0.85(3H, m), 1.25(22H, m), 3.52(2H, m), 3.91(3H, m), 4.72(1H, d, 1Hz) |
| 1-8 | $-(CH_2)_{13}Me$ | 1, 2 | 126–127 | 0.85(3H, m), 1.25(24H, m), 3.51(2H, m), 3.90(3H, m), 4.74(1H, d, 1Hz) |
| 1-9 | $-(CH_2)_{14}Me$ | 1, 2 | 126–127 | 0.85(3H, m), 1.26(26H, m), 3.45(2H, m), 3.86(3H, m), 4.73(1H, d, 1Hz) |
| 1-10 | $-(CH_2)_{15}Me$ | 1, 2 | 128–129 | 0.86(3H, m), 1.24(28H, m), 3.59(2H, m), 3.94(3H, m), 4.75(1H, d, 1Hz) |
| 1-11 | $-(CH_2)_{16}Me$ | 1, 2 | 127–129 | 0.86(3H, m), 1.27(30H, m), 3.54(2H, m), 3.86(3H, m), 4.71(1H, d, 1Hz) |
| 1-12 | $-(CH_2)_{17}Me$ | 1, 2 | 127–128 | 0.85(3H, m), 1.26(32H, m), 3.51(2H, m), 3.91(3H, m), 4.75(1H, d, 1Hz) |

TABLE 9-continued

| Compound | R¹ | Ex. No. depended | m.p. (°C.) | NMR |
|---|---|---|---|---|
| 1-13 | —(CH$_2$)$_{19}$Me | 1, 2 | 126–127 | 0.85(3H, m), 1.23(36H, m), 3.45(2H, m), 3.86(3H, m), 4.70(1H, d, 1Hz) |
| 1-14 | —(CH$_2$)$_{21}$Me | 1, 2 | 125–127 | 0.86(3H, m), 1.24(40H, m), 3.46(2H, m), 3.86(3H, m), 4.70(1H, s) |
| 1-15 | —(CH$_2$)$_{10}$COOMe | 1 | 78–79 | 1.26(16H, m), 2.26(2H, t, 7Hz), 3.45(2H, m), 3.54(3H, m), 4.73(1H, s) |
| 1-16 | —(CH$_2$)$_9$OH | 1 | 73–74 | 1.30(16H, m), 3.45(4H, m), 3.80(3H, m), 4.73(1H, s) |
| 1-17 | —Bz | 1 | 126–127 | 3.44(2H, m), 3.78(1H, m), 4.74(1H, s), 4.96(2H, s), 7.38(5H, m) |
| 1-18 | —(CH$_2$)$_3$Ph | 1 | 107–108 | 1.92(2H, m), 2.67(2H, m), 3.48(2H, m), 3.77(1H, m), 3.92(2H, t, 7Hz), 4.77(1H, s), 7.23(5H, m) |
| 1-19 | 4-Br—Bz | 1 | 184–185 | 3.45(3H, m), 3.76(1H, m), 4.75(1H, s), 4.92(2H, s), 7.36(2H, d, 8Hz), 7.54(2H, d, 8Hz) |
| 1-20 | 4-Cl—Bz | 1 | 174–175 | 3.55(2H, m), 3.84(1H, m), 4.75(1H, s), 4.98(2H, s), 7.38(4H, m) |
| 1-21 | 4-Me—Bz | 1 | 157–158 | 2.28(3H, s), 3.45(2H, m), 3.75(1H, m), 4.73(1H, s), 4.90(2H, s), 7.14(2H, d, 7Hz), 7.31(2H, 7Hz) |
| 1-22 | 3-Me—Bz | 1 | 92–93 | 2.30(3H, s), 3.44(2H, m), 3.77(1H, m), 4.75(1H, d, 1Hz), 4.92(2H, s), 7.20(4H, m) |
| 1-23 | 4-iPr—Bz | 1 | 118–119 | 1.20(6H, d, 7Hz), 3.87(1H, hep, 7Hz), 3.45(2H, m), 3.76(1H, m), 4.73(1H, s), 4.71(2H, s), 7.27(4H, m) |
| 1-24 | 4-COOMe—Bz | 1 | 171–172 | 3.44(2H, m), 3.75(2H, m), 3.84(3H, s), 4.74(1H, s), 5.03(2H, s), 7.55(2H, d, 7Hz), 7.95(2H, d, 7Hz) |
| 1-25 | —CH$_2$—C$_6$H$_4$—CH=CH—COOEt | 1 | 158–160 | 1.28(3H, t, 7Hz), 3.46(2H, m), 3.81(1H, m), 4.22(2H, q, 7Hz), 4.78(1H, s), 5.22,(2H, s), 6.22(1H, d, 16Hz), 7.49(2H, d, 8Hz), 7.62(1H, d, 16Hz), 7.72(2H, m) |
| 1-26 | —(CH$_2$)$_2$CH(Ph)$_2$ | 1 | 129–130 | 2.37(2H, m), 3.45(2H, m), 3.78(3H, m), 4.17(1H, t, 7Hz), 4.74(1H, d, 1Hz), 7.26(10H, m) |
| 1-27 | —(CH$_2$)$_8$OCH$_2$Ph | 1 | 75–76 | 1.29(12H, m), 3.40(4H, m), 3.87(3H,), 4.42(2H, s), 4.74(1H, s), 7.29(5H, s) |
| 1-28 | —CH$_2$-Cyclohexyl | 1 | 125–126 | 1.25(6H, m), 1.63(7H, m), 3.37(2H, m), 3.62(3H, m), 4.64(1H, s), |
| 1-29 | -Phenacyl | 1 | 145–146 | 3.43(2H, m), 3.78(1H, m), 4.76(1H, s), 5.33(2H, s), 7.58(3H, m), 7.89(2H, m) |
| 1-30 | —CH$_2$—C$_6$H$_4$—O—(CH$_2$)$_5$CH$_3$ | 1 | 133–134 | 0.88(3H, m), 1.33(8H, m), 3.45(2H, m), 3.73(1H, m), 3.93(2H, t, 7Hz), 4.72(1H, d, 1Hz), 4.86(2H, s), 6.84(2H, d, 8Hz), 7.32(2H, d, 8Hz) |
| 1-31 | —CH$_2$CON(morpholino) | 2 | Oil | 3.56(11H, m), 4.40(1H, m), 4.56(2H, m), 4.64(1H, d, 2Hz) |

TABLE 9-continued

| Compound | R¹ | Ex. No. depended | m.p. (°C.) | NMR |
|---|---|---|---|---|
| 1-32 | —CH$_2$CON(cyclohexyl with COOMe) | 2 | Oil | 1.95(4H, m), 3.44(5H, m), 3.62(3H, s), 4.35(1H, m), 4.60(1H, m), 4.74(1, d, 2Hz) |
| 1-33 | —CH$_2$—(naphthyl) | 1 | Oil | 3.66(5H, m), 4.74(1H, d, 2Hz), 5.40(2H, m), 7.45 (7H, m) |
| 1-34 | —(CH$_2$)$_8$CH=CH(CH$_2$)$_7$CH$_3$ | 1 | 101–104 | 0.86(3H, m), 1.25(22H, m), 1.98(4H, m), 2.80(5H, m), 4.69(1H, d, 2Hz), 5.21 (2H, t, 6Hz) |
| 1-35 | —CH$_2$COOCH$_3$ | 1 | Oil | 3.54(3H, m), 3.65(3H, s), 3.88(5H, m), 4.67 (1H, d, 2Hz) |
| 1-36 | —(CH$_2$)$_4$COOCH$_3$ | 1 | Oil | 1.70(4H, m), 2.35(2H, m), 3.65(3H, s), 3.88 (5H, m), 4.67(1H, d, 2Hz) |
| 1-37 | —(CH$_2$)$_{10}$-(2,5-dimethoxy-3-methyl-1,4-benzoquinone) | 2 | Oil | 1.28(16H, m), 2.12(3H, s), 2.57(2H, m), 3.90 (5H, m), 3.85(6H, s) |
| 1-38 | —(CH$_2$)$_4$CH=CH-(3-pyridyl, phenyl) | 1 | Oil | 1.46(6H, m), 2.10(2H, m), 3.80(5H, m), 4.63(1H, d, 2Hz), 6.10(1H, t, 7Hz), 7.38(7H, m), 8.45(2H, m) |

Incidentally, the compound (1-37) was obtained by subjecting a hydroquinone compound, prepared after conducting a procedure analogous to Example 2, to oxidation with ferric chloride.

EXAMPLE 4

(1) To a solution of 2-octadecyl-L-ascorbic acid (0.8 g, 2 mmole) in chloroform (20 ml) were added pyridine (1 ml) and 4,4-dimethylaminopyridine (0.1 g), followed by adding acetyl chloride (0.25 ml) at room temperature. The reaction solution was stirred for 18 hours, then the organic layer was washed with 2N hydrochloric acid, followed by washing with water and drying. The solvent was evaporated off under reduced pressure, and the product was recrystallized from isopropyl ether - ethyl acetate to give 6-O-acetyl-2-O-octadecyl-L-ascorbic acid (0.6 g, 65%), m.p. 117°–118° C. C$_{26}$H$_{40}$O$_7$ (Found: C,66.24; H,9.95%. Anal. Calcd: C,66.35; H,9.85).

(2) By a procedure analogous to the above, 2-O-pentadecyl-L-ascorbic acid, 2-O-hexadecyl-L-ascorbic acid and 2-O-octadecyl-L-ascorbic acid were respectively subjected to acetylation, benzoylation, phenyl-acetylation and succinylation to give the following compounds.

(i) 6-O-Acetyl-2-O-pentadecyl-L-ascorbic acid, m.p. 112°–113° C. C$_{23}$H$_{40}$O$_7$ (Found: C,64.59; H,9.48%. Anal. Calcd: C,64.46; H,9.41)

(ii) 6-O-Benzoyl-2-O-pentadecyl-L-ascorbic acid, m.p. 139°–140° C. C$_{28}$H$_{42}$O$_7$ (Found: C,68.36; H,8.78%. Anal. Calcd: C,68.55; H,8.63)

(iii) 6-O-Phenylacetyl-2-O-pentadecyl-L-ascorbic acid, m.p. 126°–127° C. C$_{29}$H$_{44}$O$_7$ (Found: C,68.79; H,8.99%. Anal. calcd: C,69.02; H,8.79)

(iv) 6-O-Acetyl-2-O-hexadecyl-L-ascorbic acid, m.p. 114°–115° C. C$_{24}$H$_{42}$O$_7$ (Found: C,65.02; H,9.46%. Anal. Calcd: C,65.13; H,9.56)

(v) 6-O-Nicotynoyl-2-O-octadecyl-L-ascorbic acid hydrochloride, m.p. 142°–143° C. C$_{34}$H$_{48}$NO$_7$Cl (Found: C,66.49; H,8.70; N,2.20%. Anal. Calcd: C,66.06; H,7.83; N,2.27)

(vi) 6-O-(3-Carboxypropionyl)-2-O-tetradecyl-L-ascorbic acid, m.p. 155°–156° C. C$_{24}$H$_{40}$O$_9$ (Found: 60.73; H,8.66%. Anal. Calcd: C, 60.99; H, 8.53)

(vii) 6-O-(3-Carboxypropionyl)-2-O-pentadecyl-L-ascorbic acid, m.p. 156°–157° C. $C_{25}H_{42}O_9$ (Found: 61.59; H, 8.87%. Anal. Calcd: C, 61.71; H, 8,70)

(viii) 6-O-(3-Carboxypropionyl)-2-O-octadecyl-L-ascorbic acid, m.p. 155°–156° C. $C_{28}H_{48}O_9$ (Found: 63.49; H,9.33%. Anal. Calcd: C, 63.61; H, 9.15)

EXAMPLE 5

To a solution of 2-O-octadecyl-L-ascorbic acid (0.8 g, 2 mmole) in chloroform (20 ml) was added pyridine (1 ml). To the mixture was added dropwise acetyl chloride (0.25 ml) at room temperature. The reaction solution was stirred for one hour, followed by washing with 2N hydrochloric acid. The organic layer was washed with water and dried. The solvent was evaporated off under reduced pressure. The product was recrystallized from isopropyl ether - ethyl acetate to give 3-O-acetyl-2-O-actadecyl-L-ascorbic acid (0.8 g, 87%), m.p. 78°–79° C. $C_{26}H_{46}O_7$ (Found: C,66.07; H,9.80%. Anal.Calcd: C,66.35; H,9.85)

EXAMPLE 6

To a solution of 2-O-octadecyl-L-ascorbic acid (0.8 g, 2 mmole) and phenylisocyanate (0.24 g, 2 mmole) in chloroform (20 ml) was added trichloracetic acid (0.1 ml). The mixture was heated at 60° C. for one hour, which was washed with water, dried and concentrated to give a product. The product was recrystallized from isopropyl ether - ethyl acetate to give 6-O-phenylcarbamoyl-2-O-octadecyl-L-ascorbic acid (0.75 g), m.p. 149°–150° C. $C_{31}H_{49}NO_7$ (Found: C,68.14; H,9.08; N,2.74%. Anal. Calcd: C,67.98; H,9.02; N,2.56).

EXAMPLE 7

(1) To a solution of sodium D-isoascorbate 120 g, 0.1 mole) in dimethylformamide (50 ml) was added dropwise benzyl bromide (12 ml). The mixture was heated at 50° C. for 4 hours. To the reaction solution was added water (100 ml). The product was extracted with ethyl acetate. The organic layer was washed with water, dried and concentrated. Then, the crude product was subjected to silica-gel chromatography and developed with ethyl acetate to give 2-O-benzyl-D-isoascorbic acid (10 g, 37%). This benzyl compound(10 g, 0.037 mole) was dissolved in a mixture of dimethyl sulfoxide (40 ml) and tetrahydrofuran (10 ml). The solution was allowed to react with octadecyl iodide (14 g) in the presence of potassium carbonate (5 g) at 50° C. for 2 hours. To the reaction product, after cooling, was added water (100 ml), and the product was extracted with isopropyl ether. The organic layer was washed with water, dried and concentrated under reduced pressure. The concentrate was subjected to silica-gel column chromatography, followed by development with isopropyl ether: ethyl acetate (1:1). Thus-obtained crude crystals were recrystallized from hexane: isopropyl ether (1:1) to give 2-O-octadecyl-3-O-benzyl-D-isoascorbic acid (5 g, 26%), m.p. 62°–63° C. $C_{31}H_{50}O_8$ (Found: C,72.02; H,9.67%. Anal.Calcd: C,71.78; H,9.72)

(2) 2-O-Octadecyl-3-O-benzyl-D-isoascorbic acid obtained as above (3 g, 6.7 mmole) was dissolved in ethanol (50 ml). The solution was subjected to hydrogenation under atmospheric pressure in the presence of 5% Pd-carbon (0.2 g). Eighteen hours later, the catalyst was filtered off, and the filtrate was concentrated under reduced pressure. The concentrate was recrystallized from ethyl acetate to give 2-O-octadecyl-D-isoascorbic acid (2 g, 80%), m.p. 103°–104° C. $C_{24}H_{44}O_6$ (Found: C,67.45; H,10.46%. Anal.Calcd: C,67.26; H,10.35).

EXAMPLE 8

To a solution of 5,6-O,O-isopropylidene-3-O-methoxymethyl-2-O-octadecyl-L-ascorbic acid (5 g, 10 mmole) in tetrahydrofuran (20 ml) was added 1,8-diazabicyclo[5,4,0]-7-undecene (3 ml). The mixture was stirred at 50° C. for 2 hours. To the reaction mixture, after cooling, was added ethyl acetate (40 ml). The whole mixture was washed twice with 2N hydrochloric acid, followed by washing with water, drying and concentration under reduced pressure. The concentrate was stirred at 60° C. for 6 hours in a mixture of ethanol (40 ml) and 2N hydrochloric acid (20 ml). The reaction solution was concentrated under reduced pressure, and the product was dissolved in ethyl acetate, washed with water, dried and concentrated. The crude product thus obtained was recrystallized from isopropyl ether to give 2-O-octadecyl-5-dehydroxyascorbic acid (2 g, 51%), m.p. 114°–115° C. $C_{24}H_{42}O_5$ (Found: C,70.24; H,10.42%. Anal. Calcd: C,70.21; H,10.31).

2-O-Octadecyl-5-dehydroxyascorbic acid obtained as above (0.4 g, 1 mmole) was dissolved in ethanol (10 ml). To the solution was added 5% Pd-carbon (0.2 g), and the mixture was stirred in hydrogen atmosphere for 4 hours under normal pressure. After completion of the reaction, the catalyst was filtered off, and the filtrate was concentrated under reduced pressure. The concentrate was recrystallized from isopropyl ether - hexane to give the desired d,l-2-O-octadecyl-5-deoxyascorbic acid (0.2 g), m.p. 83°–84° C. $C_{24}H_{44}O_5$ (Found: C,69.33; H,10.74%. Anal. Calcd: C,69.86; H,10.75).

EXAMPLE 9

By using the following ingredients, tablets are prepared by per se conventional means.

| | |
|---|---|
| Compound (1–12) [Compound [I] wherein $R^1 = (CH_2)_{17}CH_3$ $R^2 = OH, R^3 = H$] | 50 mg |
| Corn starch | 90 mg |
| Lactose | 30 mg |
| Hydroxypropyl cellulose L | 25 mg |
| Magnesium stearate | 5 mg |
| Total | 200 mg (per tablet) |

Dosage is 1–3 tablets/adult after each meal (three times/day).

EXAMPLE 10

By using the following ingredients, tablets are prepared by per se conventional means.

| | |
|---|---|
| Compound (1–9) [Compound [I] wherein $R^1 = (CH_2)_{14}CH_3$, $R^2 = OH, R^3 = H$] | 60 mg |
| Corn starch | 80 mg |
| Lactose | 30 mg |
| Hydroxypropyl cellulose L | 25 mg |
| Magnesium stearate | 5 mg |
| Total | 200 mg |

Dosage is 1–3 tablets/adult after each meal (three times/day).

EXAMPLE 11

(1) To a solution of 2-O-octadecyl-L-ascorbic acid (0.8 g, 2 mmol) in acetone(50 ml) was added p-toluenesulfonic acid (50 mg). The mixture was stirred at room temperature for 6 hours. To the reaction solution was added sodium hydrogencarbonate (100 mg), which was then concentrated under reduced pressure. The resulting crude crystals were recrystallized from diisopropyl ether (IPE) to give 2-O-octadecyl-5,6-O,O-isopropylidene-L-ascorbic acid (0.8 g, 91%), m.p. 81°-82° C.

(2) 2-O-Dodecyl-L-ascorbic acid and 2-O-hexadecyl-L-ascorbic acid were respectively subjected to a reaction analogous to the above to give the compounds shown below, respectively.

(i) 2-O-Dodecyl-5,6-O,O-isopropylidene-L-ascorbic acid, m.p. 83°-84° C.

(ii) 2-O-Hexadecyl-5,6-O,O-isopropylidene-L-ascorbic acid, m.p. 85°-86° C.

EXAMPLE 12

(1) To a solution of 2-O-hexadecyl-L-ascorbic acid (0.8 g, 2 mmol) and cyclohexanone (0.3 g) in toluene (50 ml) was added p-toluenesulfonic acid (50 mg). While the mixture was refluxed, the water then produced was separated. The reaction solution, after cooling, was washed with an aqueous solution of saturated sodium hydrogencarbonate, followed by drying and concentration under reduced pressure to give crude crystals, which were recrystallized from IPE to give 2-O-hexadecyl-5,6-O,O-cyclohexylidene-L-ascorbic acid (0.6 g, 84%), m.p. 80°-81° C.

(2) 2-O-Dodecyl-L-ascorbic acid was subjected to a reaction analogous to the above to give the following compound.

(i) 2-O-Dodecyl-5,6-O,O-cyclohexylidene-L-ascorbic acid, m.p. 85°-86° C.

What is claimed is:

1. A pharmaceutical composition for treatment of prophylaxis or improvement of disorders in functions of the circulatory system caused by biologically activated oxygen species and reactive organic radicals, which composition contains in an amount for administering 0.1 mg/kg to 50 mg/kg of an ascorbic acid derivative of the formula:

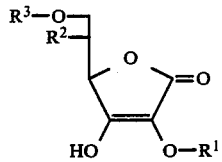

wherein $R^1$ is of the formula —$CH_2$—R, wherein R is a $C_{5-22}$ straight-chain or branched alkyl;

a $C_{1-10}$ straight-chain or branched-chain alkyl group having one to three substituents selected from the group consisting of (1) $C_{1-6}$ alkoxycarbonyl, (2) phenyl or naphthyl optionally substituted with one to three substituents selected from the group consisting of $C_{1-5}$ alkyl, $C_{1-3}$ alkoxy, halogen, nitro, amino, oxo, hydroxyl and benzyloxy, (3) benzyl or phenethyl optionally substituted with one to three substituents selected from the group consisting of $C_{1-5}$ alkyl, $C_{1-3}$ alkoxy, halogen, nitro, amino, oxo, hydroxyl and benzyloxy, (4) phenylcarbonyloxy or naphthylcarbonyloxy optionally substituted with one to three substituents selected from the group consisting of $C_{1-5}$ alkyl, $C_{1-3}$ alkoxy, halogen, nitro, amino, oxo, hydroxyl and benzyloxy, (5) benzylcarbonyloxy or phenethylcarbonyloxy optionally substituted with one to three substituents selected from the group consisting of $C_{1-5}$ alkyl, $C_{1-3}$ alkoxy, halogen, nitro, amino, oxo, hydroxyl and benzyloxy, (6) 2,3,5-trimethyl-1,4-benzoquinonyl, (7) 2,3-dimethoxy-5-methyl-1,4-benzoquinonyl and (8) 2-methyl-1,4-naphthoquinonyl;

a $C_{2-20}$ alkenyl group having one to three substituents selected from phenyl, naphthyl, benzyl or phenethyl, 3-pyridyl, thienyl and furyl;

a phenyl, naphthyl, benzyl or phenethyl optionally substituted with one to three substituents selected from the group consisting of $C_{1-5}$ alkyl, methoxy, methylenedioxy and hydroxyl;

a $C_{1-9}$ acyl group selected from the group consisting of formyl, acetyl, propionyl, n-butyryl, isobutyryl, benzoyl, morpholino-carbonyl, $C_{1-3}$ alkoxycarbonyl pyrrolidinocarbonyl, $C_{1-3}$ alkoxycarbonyl, phenylcarbonyl or naphthylcarbonyl optionally substituted with one to three substituents selected from the group consisting of hydroxyl, $C_{1-5}$ alkyl and $C_{1-3}$ alkoxy, benzylcarbonyl or phenethylcarbonyl optionally substituted with one to three substituents selected from the group consisting of hydroxyl, $C_{1-5}$ alkyl and $C_{1-3}$ alkoxy;

a phenyloxy, naphthyloxy, benzyloxy or phenethyloxy optionally substituted with one to three substituents selected from the group consisting of hydroxyl, $C_{1-5}$ alkyl and $C_{1-3}$ alkoxy;

$R^2$ is hydrogen or hydroxy; and $R^3$ is hydrogen, or acyl,; or $R^2$ and $R^3$ may together form an O,O-isopropylidene residue;

or a pharmaceutically acceptable salt thereof, and a pharmaceutically acceptable carrier, vehicle or diluent therefor.

2. The composition according to claim 1, wherein $R^3$ is acyl.

3. The composition according to claim 1, wherein $R_1$ is a $C_{1-10}$ straight-chain or branched-chain alkyl group which has one to three substituent(s), the substituent being the class consisting of (1) $C_{1-6}$ alkoxycarbonyl, (2) phenyl or naphthyl which may have one to three substituents(s) of the class consisting of $C_{1-5}$ alkyl, $C_{1-3}$ alkoxy, halogen, nitro, amino, oxo, hydroxyl and benzyloxy, (3) benzyl or phenethyl which may have one to three substituents(s) of the class consisting of $C_{1-5}$ alkyl, $C_{1-3}$ alkoxy, halogen, nitro, amino, oxo, hydroxyl and benzyloxy, (4) phenylcarbonyloxy or naphthylcarbonyloxy which may have one to three substituent(s) of the class consisting of $C_{1-5}$ alkyl, $C_{1-3}$ alkoxy, halogen, nitro, amino, oxo, hydroxyl and benzyloxy, (5) benzylcabonyloxy or phenethlcarbonyloxy which may have one to three substituent(s) of the class consisting of $C_{1-5}$ alkyl, $C_{1-3}$ alkoxy, halogen, nitro, amino, oxo, hydroxyl and benzyloxy, (6) 2,3,5-trimethyl-1,4-benzoquinonyl, (7) 2,3-dimethoxy-5-methyl-1,4-benzoquinonyl and (8) 2-methyl-1,4-naphthoquinonyl.

4. The composition according to claim 1, wherein $R_1$ is a $C_{2-20}$ alkenyl group which may have one to three substituent(s), the substituent being the class consisting of phenyl, naphthyl, benzyl, phenethyl, 3-pyridyl, thienyl and furyl.

5. The composition according to claim 1, wherein $R_1$ is a phenyl, naphthyl, benzyl, or phenethyl group which may have one to three substituent(s), the substituent being the class consisting of $C_{1-5}$ alkyl, methoxy, methylenedioxy and hydroxyl.

6. The composition according to claim 1, wherein $R_1$ is a $C_{1-9}$ acyl group of the class consisting of formyl, acetyl, propionyl, n-butyryl, isobutyryl, benzoyl, morpholinocarbonyl, $C_{1-3}$ alkoxycarbonylpyrrolidinocarbonyl, $C_{1-3}$ alkoxycarbonyl, phenylcarbonyl or naphthylcarbonyl which have one to three substituent(s) of the class consisting of hydroxyl group, $C_{1-5}$ alkyl and $C_{1-3}$ alkoxy, or benzylcarbonyl or phenethylcarbonyl which have one to three substituent(s) of the class consisting of hydroxyl group, $C_{1-5}$ alkyl and $C_{1-3}$ alkoxy.

7. The composition according to claim 1, wherein $R_1$ is phenyloxy, naphthyloxy, benzyloxy, or phenethyloxy group which may have one to three substituent(s), the substituent being the class consisting of hydroxyl group, $C_{1-5}$ alkyl group and $C_{1-3}$ alkoxy group.

8. The composition according to claim 1, wherein $R^1$ is —$(CH_2)_{10}COOCH_3$, $R^2$ is hydroxyl and $R^3$ is hydrogen.

9. The composition according to claim 1, wherein $R^1$ is —$(CH_2)_{17}CH_3$, $R^2$ is hydroxyl and $R^3$ is nicotynoyl.

10. A method of treatment of prophylaxis or improvement of disorders in functions of the circulatory system caused by biologically activated oxygen species and reactive organic radicals, which comprises administering to a mammal an effective amount of an ascorbic acid derivative of the formula:

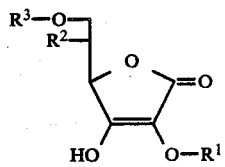

wherein
$R^1$ is of the formula —$CH_2$—R, wherein R is $C_{5-22}$ straight-chain or branched alkyl;
a $C_{1-10}$ stright-chain or branched-chain alkyl group having one to three substituents selected from the group consisting of (1) $C_{1-6}$ alkoxycarbonyl, (2) phenyl or naphthyl optionally substituted with one to three substituents selected from the group consisting of $C_{1-5}$ alkyl, $C_{1-3}$ alkoxy, halogen, nitro, amino, oxo, hydroxyl and benzyloxy, (3) benzyl or phenethyl optionally substituted with one to three substituents selected from the group consisting of $C_{1-5}$alkyl, $C_{1-3}$ alkoxy, halogen, nitro, amino, oxo, hydroxyl and benzyloxy, (4) phenylcarbonyloxy or naphthylcarbonyloxy optionally substituted with one to three substituents selected from the group consisting of $C_{1-5}$ alkyl, $C_{1-3}$ alkoxy, halogen, nitro, amino, oxo, hydroxyl and benzyloxy, (5) benzylcarbonyloxy or phenethylcarbonyloxy optionally substituted with one to three substituents selected from the group consisting of $C_{1-5}$ alkyl, $C_{1-3}$ alkoxy, halogen, nitro, amino, oxo, hydroxyl and benzyloxy, (6) 2,3,5-trimethyl-1,4-benzoquinonyl, (7) 2,3-dimethoxy-5-methyl-1,4-benzoquinonyl and (8) 2-methyl-1,4-napthoquinonyl;
a $C_{2-20}$ alkenyl group having one to three substituents selected from phenyl, naphthyl, benzyl, phenethyl, 3-pyridyl, thienyl and furyl;
a phenyl, napthyl, benzyl or phenethyl optionally substituted with one to three substituents selected from the group consisting of $C_{1-5}$ alkyl, methoxy, methylenedioxy and hydroxyl;
a $C_{1-9}$ acyl group selected from the group consisting of formyl, acetyl, propionyl, n-butyryl, isobutyryl, benzoyl, morpholino-carbonyl, $C_{1-3}$ alkoxycarbonylpyrrolininocarbonyl, $C_{1-3}$ alkoxycarbonyl, phenylcarbonyl or naphthylcarbonyl optionally substituted with one to three substituents selected from the group consisting of hydroxyl, $C_{1-5}$ alkyl and $C_{1-3}$ alkoxy, benzylcarbonyl or phenethylcarbonyl optionally substituted with one to three substituents selected from the group consisting of hydroxyl, $C_{1-5}$ alkyl and $C_{1-3}$ alkoxy;
a phenyloxy, naphthyloxy, benzyloxy or phenethyloxy optionally substituted with one to three substituents selected from the group consisting of hydroxyl, $C_{1-5}$ alkyl and $C_{1-3}$ alkoxy;
$R^2$ is hydrogen or hydroxy; and
$R^3$ is hydrogen, or acyl; or $R^2$ and $R^3$ may together form an O,O-isopropylidene residue;
or a pharmaceutically acceptable salt thereof.

11. A method of claim 10, wherein $R^1$ is straight-chain or branched alkyl having 1 to 10 carbon atoms optionally substituted with a member selected from a group consisting of hydroxyl, carboxyl, aminocarbonyl, vinyl, ethynyl, and quinonylmethyl.

12. A method of claim 10, wherein $R^1$ is straight-chain alkyl having 9 to 20 carbon atoms.

13. A method of claim 10, wherein $R^2$ is hydroxyl.

14. A method of claim 10, wherein $R^3$ is hydrogen.

15. A method of claim 10, wherein $R^3$ and hydroxyl or $R^2$ form O,O-isopropylidene residue.

16. A method of claim 10, wherein $R^1$ is —$(CH_2)_{17}CH_3$, $R^2$ is hydroxyl and $R^3$ is hydrogen.

17. A method of claim 10, wherein the disorder in functions of the circulatory system is ischemic heart disease, ischemic cerebral disease, ischemic renal disturbance or ischemic gastrointestinal ulcers.

18. A composition of claim 1, wherein said tablet contains 10 mg to 300 mg of the ascorbic acid derivative.

* * * * *